(12) United States Patent
Van Dam et al.

(10) Patent No.: US 7,097,809 B2
(45) Date of Patent: Aug. 29, 2006

(54) COMBINATORIAL SYNTHESIS SYSTEM

(75) Inventors: Michael Van Dam, Pasadena, CA (US); Marc A. Unger, South San Francisco, CA (US); Stephen R. Quake, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 76 days.

(21) Appl. No.: 10/116,761

(22) Filed: Apr. 3, 2002

(65) Prior Publication Data

US 2003/0008411 A1    Jan. 9, 2003

Related U.S. Application Data

(63) Continuation-in-part of application No. 09/679,432, filed on Oct. 3, 2000, now Pat. No. 6,508,988.

(51) Int. Cl.
| | |
|---|---|
| G01N 15/06 | (2006.01) |
| G01N 33/00 | (2006.01) |
| G01N 33/48 | (2006.01) |
| B01L 3/02 | (2006.01) |
| B32B 5/02 | (2006.01) |

(52) U.S. Cl. .......................... 422/100; 422/50; 422/55; 422/57; 422/58; 422/61; 422/68.1; 422/81; 422/82; 422/82.01; 422/82.02; 422/82.05; 422/101; 422/102; 422/103; 422/104; 436/174; 436/178; 436/180; 436/63; 436/2; 436/8; 436/68; 436/501; 436/66

(58) Field of Classification Search .................. 422/50, 422/55, 57, 58, 61, 68.1, 81, 82, 82.01, 82.02, 422/82.05, 100, 101, 102, 103, 104; 436/174, 436/178, 180, 2, 8, 501, 63, 66, 68
See application file for complete search history.

(56) References Cited

U.S. PATENT DOCUMENTS

| | | |
|---|---|---|
| 3,570,515 A | 3/1971 | Kinner |
| 3,747,628 A | 7/1973 | Holster et al. |
| 4,046,159 A | 9/1977 | Pegourie |
| 4,119,368 A | 10/1978 | Yamazaki |

(Continued)

FOREIGN PATENT DOCUMENTS

EP    0 592 094 A2    4/1994

(Continued)

OTHER PUBLICATIONS

E. M. Southern et al., *Geonomics*, 1992, 13, 1008-1017.

(Continued)

*Primary Examiner*—Jill Warden
*Assistant Examiner*—Brian Sines
(74) *Attorney, Agent, or Firm*—Townsend and Townsend and Crew LLP

(57) ABSTRACT

The present invention provides a microfluidic device for synthesizing an array of compounds and methods for using the same. In particular, the microfluidic device of the present invention comprises a solid support base, an elastomeric layer attached to the solid support, and a plurality of flow channels located within the interface between the solid support and the elastomeric layer. In addition, the solid support comprises a functional group for forming a bond with a reactive reagent. In some embodiments, the microfluidic device further comprises a second plurality of flow channels that intersect the first plurality of flow channels. A plurality of control channels are also present in the microfluidic devices of the present invention. The control channels can be actuated to regulate flow of fluids within the flow channel(s).

15 Claims, 18 Drawing Sheets

U.S. PATENT DOCUMENTS

| | | | |
|---|---|---|---|
| 4,153,855 A | 5/1979 | Feingold | |
| 4,245,673 A | 1/1981 | Bouteille et al. | |
| 4,434,704 A | 3/1984 | Surjaatmadja | |
| 4,898,582 A | 2/1990 | Faste | |
| 4,992,312 A | 2/1991 | Frisch | |
| 5,085,562 A | 2/1992 | Van Lintel | |
| 5,088,515 A | 2/1992 | Kamen | |
| 5,096,388 A | 3/1992 | Weinberg | |
| 5,126,115 A | 6/1992 | Fujita et al. | |
| 5,164,558 A | 11/1992 | Huff et al. | |
| 5,171,132 A | 12/1992 | Miyazaki et al. | |
| 5,224,843 A | 7/1993 | Van Lintel | |
| 5,259,737 A | 11/1993 | Kamisuki et al. | |
| 5,265,327 A | 11/1993 | Faris et al. | |
| 5,290,240 A | 3/1994 | Horres, Jr. | |
| 5,336,062 A | 8/1994 | Richter | |
| 5,346,372 A | 9/1994 | Naruse et al. | |
| 5,375,979 A | 12/1994 | Trah | |
| 5,376,252 A | 12/1994 | Ekström et al. | |
| 5,400,741 A | 3/1995 | DeTitta et al. | |
| 5,423,287 A | 6/1995 | Usami et al. | |
| 5,529,465 A | 6/1996 | Zengerle et al. | |
| 5,593,130 A | 1/1997 | Hansson et al. | |
| 5,642,015 A | 6/1997 | Whitehead et al. | |
| 5,659,171 A | 8/1997 | Young et al. | |
| 5,660,370 A | 8/1997 | Webster | |
| 5,681,024 A | 10/1997 | Lisec et al. | |
| 5,681,484 A | 10/1997 | Zanzucchi et al. | |
| 5,705,018 A | 1/1998 | Hartley | |
| 5,759,014 A | 6/1998 | Van Lintel | |
| 5,775,371 A | 7/1998 | Pan et al. | |
| 5,788,468 A | 8/1998 | Dewa et al. | |
| 5,836,750 A | 11/1998 | Cabuz | |
| 5,842,787 A | 12/1998 | Kopf-Sill et al. | |
| 5,858,188 A | 1/1999 | Soane et al. | |
| 5,866,345 A | 2/1999 | Wilding et al. | |
| 5,875,817 A | 3/1999 | Carter | |
| 5,876,187 A | 3/1999 | Afromowitz et al. | |
| 5,885,837 A | 3/1999 | Winkler et al. | |
| 5,922,591 A * | 7/1999 | Anderson et al. | 435/287.2 |
| 5,932,799 A | 8/1999 | Moles | |
| 5,942,443 A | 8/1999 | Parce et al. | |
| 6,007,309 A | 12/1999 | Hartley | |
| 6,043,080 A | 3/2000 | Lipshutz et al. | |
| 6,123,769 A | 9/2000 | Sanjoh | |
| 6,155,282 A | 12/2000 | Zachary et al. | |
| 6,174,365 B1 | 1/2001 | Sanjoh | |
| 6,186,660 B1 | 2/2001 | Kopf-Sill et al. | |
| 6,261,431 B1 | 7/2001 | Mathies et al. | |
| 6,264,892 B1 | 7/2001 | Kaltenbach et al. | |
| 6,296,673 B1 | 10/2001 | Santarsiero et al. | |
| 6,345,502 B1 | 2/2002 | Tai et al. | |
| 6,408,878 B1 * | 6/2002 | Unger et al. | 137/597 |
| 6,409,832 B1 | 6/2002 | Weigl et al. | |
| 6,454,924 B1 * | 9/2002 | Jedrzejewski et al. | 204/601 |
| 6,767,706 B1 | 7/2004 | Quake et al. | |
| 2001/0027745 A1 | 10/2001 | Weigl et al. | |
| 2002/0037499 A1 | 3/2002 | Quake et al. | |

FOREIGN PATENT DOCUMENTS

| | | |
|---|---|---|
| EP | 0 703 364 A1 | 3/1996 |
| EP | 0 706 004 A2 | 4/1996 |
| EP | 0 779 436 A2 | 6/1997 |
| EP | 0 829 360 A2 | 3/1998 |
| EP | 0 845 603 A1 | 6/1998 |
| EP | 0 999 055 A2 | 5/2000 |
| GB | 2 155 152 A | 9/1985 |
| GB | 2 308 460 A | 6/1997 |
| WO | WO 98/07069 A1 | 2/1998 |
| WO | WO 99/00655 A2 | 1/1999 |
| WO | WO 99/04361 A1 | 1/1999 |
| WO | WO 99/17093 A1 | 4/1999 |
| WO | WO 99/52633 A1 | 10/1999 |
| WO | WO 00/00678 A1 | 1/2000 |
| WO | WO 00/43748 A1 | 7/2000 |
| WO | WO 00/60345 A1 | 10/2000 |
| WO | WO 01/09595 A2 | 2/2001 |
| WO | WO 01/09595 A3 | 2/2001 |

OTHER PUBLICATIONS

Edwin M. Southern et al., *Journal of Biotechnology*, 1994, 35, 217-227.

G. Wallraff et al., *Chemtech*, 1997, 22-32.

R. Michael van Dam et al., *Genome Research*, 145-152.

Ahn et al., "Fluid Micropumps Based on Rotary Magnetic Actuators," Proceedings of 1995 IEEE Micro Electro Mechanical Systems Workshop (MEMS '95), held in Amsterdam, Netherlands on Jan. 29-Feb. 2, 1995, pp. 408-412.

Benard et al., "A Titanium—Nickel Shape-Memory Alloy Actuated Micropump," Proceedings of Transducers '97, 1997 International Conference on Solid-State Sensors and Actuators, held in Chicago, Il., Jun. 16-19, 1997, 1:361-364 (1997).

Brechtel et al.; "Control of the electroosmotic flow by metal-salt-containing buffers", J Chromatography A, 1995, pp. 97-105, vol. 716.

Bryzek et al.; "Micromachines on the March", IEEE Spectrum, 1994, pp. 20-31, vol. 31, No. 5.

Buchaillot et al.; "Silicon nitride thin films Young's modulus determination by an optical non-destructive method", Jpn. J Appl Phys, 1995, pp. L794-L797, vol. 36, No. 2:6B.

Chiu et al.; "Patterned Deposition of Cells and Proteins onto Surfaces by Using Three-Dimensional Microfluidic Systems", Proc. Natl. Acad. Sci., 2000, pp. 2408-2413, vol. 97, No. 6.

Chou et al. "A microfabricated device for sizing and sorting DNA molecules", Applied Physical Sciences, Biophysics, Proc. Natl. Acad. Sci., 1999, pp. 11-13, vol. 96, U.S.A.

Delamarche et al.; "Patterned delivery of immunoglobulins to surfaces using microfluidic networks", Science, 1997, pp. 779-781, vol. 276.

Duffy et al. "Patterning Electroluminescence Materials with Feature Sizes as Small as 5 μm Using Elastomeric Membranes as Masks for Dry Lift-Off", Advanced Materials, 1999, pp. 546-552, vol. 11, No. 7.

Duffy et al. "Rapid Prototyping of Microfluidic Switches in Poly(dimethylsiloxane) and Their Actuation by Electro-Osmotic Flow" Journal of Microeng, 1999, pp. 211-217, vol. 9.

Duffy et al. "Rapid Prototyping of Microfluidic Systems in Poly(dimethylsiloxane)", Analytical Chemistry, 1998, pp. 4974-4984, vol. 70, No. 23.

Effenhauser et al.; "Integrated capillary electrophoresis on flexible silicone microdevices: Analysis of DNA restriction fragments and detection of single DNA molecules on microchips", Anal. Chem, 1997, pp. 3451-3457, vol. 69.

Effenhauser et al.; "Integrated chip-based capillary electrophoresis", Electrophoresis, 1997, pp. 2203-2213, vol. 18.

Fahrenberg et al. "A microwave system fabricated by thermoplastic molding", J Micromech Microeng, 1995, pp. 169-171, vol. 5.

Fu et al.; "A microfabricated fluorescence-activated cell-sorter", Nature Biotechnology, 1999, pp. 1109-1111, vol. 17.

Gass et al., "Integrated flow-regulated silicon micropump," Sensors and Actuators A Physical, 1994, p. 335-338, vol. 43.

Gerlach, T., "Pumping Gases by a Silicon Micro Pump with Dynamic Passive Valves," Proceedings of Transducers '97, 1997 International Conference on Solid-State Sensors and Actuators, held in Chicago, Il., Jun. 16-19, 1997, pp. 357-360, vol. 1.

Goll et al., "Microvalves with bistable buckled polymer diaphragms," J. Micromech. Microeng., 1996, pp. 77-79, vol. 6.

Gravesen et al.; "Microfluids—A Review", Journal Micromech Microeng, 1993, pp. 168-192, vol. 3.

Harrison et al., "Micromachining a Miniaturized Capillary Electrophoresis-Based Chemical Analysis System on a Chip," Science, 1993, pp. 895-897, vol. 261.

Hornbeck et al., "Bistable Deformable Mirror Device," Spatial Light Modulators and Applications 1988 Technical Digest Series, vol. 8, Postconference Edition, Summaries of papers presented at the Spatial Light Modulators and Applications Topical Meeting, Jun. 15-17, 1988, Optical Society of America, pp. 107-110.

Hosokawa et al., "Handling of Picoliter Liquid Samples in a Poly(dimethylsiloxane)-Based Microfluidic Device," Anal. Chem., 1999, 71(20):4781-4785.

Ikuta et al., "Three dimensional micro integrated fluid systems (MIFS) fabricated by stereo lithography," IEEE Kyushu Institute of Technology, 1994, pp. 1-6.

Jacobson et al., "High-speed separations on a microchip," Anal. Chem., 1994, 66(7):1114-1118.

Jacobson et al., "Microfluidic Devices for Electrokinetically Driven Parallel and Serial Mixing," Anal. Chem., 1999, 71(20):4455-4459.

Jerman, H., "Electrically-Activated, Normally-Closed Diaphragm Valves," Proceedings of Transducers '91, 1991 International Conference on Solid-State Sensors and Actuators, pp. 1045-1048 (1991).

Jung et al., "Chemical and Physical Interactions at Metal/Self-Assembled Organic Monolayer Interfaces," Critical Reviews in Solid State and Material Sciences, 1994, pp. 2-10, vol. 19, No. 1.

Kenis et al, "Microfabrication Inside Capillaries Using Multiphase Laminar Flow Patterning," Science, 1999, 285:83-85.

Kim, Enoch et al., "Micromolding in Capillaries: Applications in Material Science," J. American Chemical Society, 118:5722-5731 (1996).

Kopp et al. "Chemical Amplification: Continuous-Flow PCR on a Chip", Science, 1998, 280:1046-1048.

Kuhn et al. "Silicon Charge Electrode Array for Ink Jet Printing", IEEE Transactions on Electron Devices, 1978, pp. 1257-1260, vol. ED-25, No. 10.

Lin et al. "Free-Space Micromachined Optical Switches for Optical Networking," IEEE J. Selected Topics in Quantum Electronics, 1999, pp. 4-9, vol. 5, No. 1.

Lötters et al. "The mechanical properties of the rubber elastic polymer polydimethylsiloxane for sensor applications," J. Micromech. Microeng., 1997, 7:145-147.

Lucy et al., "Characterization of the Cationic Surfactant Induced Reversal of Electroosmotic Flow in Capillary Electrophoresis," Anal. Chem., 1996, pp. 300-305, vol. 68.

Maluf, N., An Introduction to Microelectromechanical Systems Engineering, Artech House Publishers, Boston London pp. 42-45.

Muller et al., "Surface-Micromachined Microoptical Elements and Systems," Proceedings of IEEE, 1998, 86(8):1705-1720.

Olsson et al., "Simulation Studies of Diffuser and Nozzle Elements for Valve-less Micropumps," Proceedings of Transducers '97, 1997 International Conference on Solid-State Sensors and Actuators, held in Chicago, Il., Jun. 16-19, 1997, 2:1039-1042 (1997).

Pethig & Markx "Applications of dielectrophoresis in biotechnology," Tibtech, 15:426-432 (1997).

Qin et al., "Photolithography with transparent reflective photomasks," J. Vac.Sci. Technology, 16(1):98-103 (1998).

Qin et al., "Elastomeric Light Valves**", Adv. Mater., 1997, pp. 407-410, vol. 9, No. 5.

Quake S.R. and Scherer A.; "From Micro- to Nanofacrication with Soft Materials", Science, Nov. 24, 2000; pp. 1536-1540, vol. 290, No. 5496.

Rapp. R., "LIGA micropump for gases and liquids," Sensors and Actuators A, 1994, pp. 57-61, vol. 40.

Roylance et al., "A Batch-Fabricated Silicon Accelerometer", IEEE Transactions on Electron Devices, Dec. 1979, pp. 1911-1917, vol. ED-26, No. 12.

Schasfoort et al., "Field-Effect Flow Control for Microfabricated Fluidic Networks," Science, 1999, 286:942-945.

Schueller et al., "Fabrication of glassy carbon microstructures by soft lithography," Sensors and Actuators, 72(2):125-139 (1999).

Shoji et al.; "Smallest Dead Volume Microvalves for Integrated Chemical Analyzing Systems", Proceedings of Transducers '91, 1991, pp. 1052-1055, San Francisco.

Shoji, S., "Fluids for Sensor Systems", Topics in Current Chemistry, 1998, pp. 162-188, vol. 194, Springer Verlag Berlin Heidelberg.

Smits, J.G., "Piezoelectric Micropump with Three Valves Working Peristaltically", Sensors and Actuators, 1990, pp. 203-206, vol. A21-A23.

Sohn et al., "Capacitance cytometry: Measuring biological cells one by one," PNAS, 97(20):10687-10690 (2000).

Tufte et al., "Silicon Diffused-Element Piezoresistive Diaphragms," J. Appl. Phys., Nov. 1962, pp. 3322-3327, vol. 33, No. 11.

Ullmann's Encyclopedia of Industrial Chemistry, Sections 6 to 6.3, Topic: Carbon Black, Sixth Edition, 1999.

Unger, Marc A. et al. "Monolithic Microfabricated Valves and Pumps by Multilayer Soft Lithography" Science, Aug. 7, 2000, vol. 288, 113-116.

Van de Pol et al., "Micro Liquid Handling Devices—A Review", Micro Systems Technologies, 1990, pp. 799-805, vol. 90.

Van de Pol, F.C.M. et al. "A Thermo-Pneumatic Actuation Principle for a Microminiature Pump and Other Micromechanical Devices" Sensors and Actuators, May 3, 1989, pp. 139-143, vol. 17, Nos. 1-2.

Vieider et al.; "A Pneumatically Actuated Micro Valve with a Silicon Rubber Membrane for Integrated with Fluid Handling Systems", Proceedings of Transducers '95, the 8th International Conference on Solid-State Sensors and Actuators and Eurosensors IX, held in Stockholm, Sweden on Jun. 25-29, 1995, pp. 284-286, Stockholm, Sweden.

Washizu et al., "Molecular Dielectrophoresis of Biopolymers," IEEE Transactions on Industry Applications, 1994, 30(4):835-843.

Xia et al., "Complex Optical Surfaces Formed by Replica Molding Against Elastomeric Masters," Science, 1996, 273:347-349.

Xia et al., "Soft Lithography," Angew. Chem. Int. Ed., 1998, 37:551-575.

Xia, Y. et al., "Micromolding of Polymers in Capillaries: Applications in Microfabrication," Chemistry of Materials, 8(7):1558-1567 (1996).

Yang et al. "A Mems Thermopneumatic Silicone Membrane Valve," Proceedings of the IEEE 10th Annual International Workshop on MicroElectro Mechanical Systems, Sensors and Actuators, 1998, A64(1):101-108.

Yang et al., "A MEMS Thermopneumatic silicone Membrane Valve," Proceedings of the IEEE 10th Annual Workshop of Micro Electro Mechanical Systems Workshop (MEMS '97), held Jan. 26-30, 1997 in Nagoya, Japan, pp. 114-118 (1997).

Yazdi et al. "Micromachined Inertial Sensors," Proceedings of IEEE, 1998, 86(8):1640-1659.

Young et al. "Contoured elastic-membrane microvalves for microfluidic network integration," J. Biomechanical Engineering, 1999, 121:2-6.

Zengerle et al., "A Micro Membrane Pump with Electrostatic Actuation," 1992 IEEE Conf. on Micro Electro Mechanical Systems, held Feb. 4-7, 1992 in Travemunde Germany, pp. 19-24.

Zengerle et al., "Performance Simulation of Microminiaturized Membrane Pumps," from 7th International Conference on Solid-State Sensors and Actuators held Jun. 7-10, 1993 in Yokohama Japan, pp. 106-109.

"Biochips," Nature Biotechnology, vol. 18, Supplement 2000, pp. IT43-IT44, 2000.

"Chapter 9: Microfluidic Devices," Micromachined Transducers Sourcebook, pp. 779-882, 1998.

"Electro Microfluidic Dual In-Line Package (EMDIP)," Sandia National Laboratories, 2 pages, no date.

Allcock, Harry R. et al., Contemporary Polymer Chemistry, Second Edition, pp. cover, 9-11, no date.

Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.

Angell, James B. et al., "Silicon Micromechanical Devices," Scientific American, pp. cover, 44-55, Apr. 1983.

Armani, Deniz et al., "Re-Configurable Fluid Circuits By PDMS Elastomer Micromachining," IEEE Int. Conf. Micro Electro Mech. Syst. Tech. Digest, vol. 12, pp. 222-227, 1999.

Ballantyne, J. P. et al., "Selective Area-Metallization By Electron-Beam Controlled Direct Metallic Deposition," J. Vac. Sci. Technol., vol. 10, No. 6, pp. 1094-1097, Nov. 1973.

Bloomstein, T. M. et al., "Laser-Chemical Three-Dimensional Writing For Microelectromechanics And Application To Standard-Cell Microfluidics," J. Vac. Sci. Technol. B, vol. 10, No. 6, pp. 2671-2674, Nov. 1992.

Bousse, Luc et al., "Electrokinetically Controlled Microfluidic Analysis Systems," Annu. Rev. Biophys. Biomol. Struct., vol. 29, pp. 155-181, 2000.

Brush, Michael, "Automated Laboratories," The Scientist, vol. 13, No. 4, 10 pages, Feb. 15, 1999.

Chou, Hou-Pu et al., "Integrated Elastomer Fluidic Lab-On-A-Chip-Surface Patterning And DNA Diagnostics," Proceedings of the Solid State Actuator and Sensor Workshop, Hilton Head, South Carolina, 4 pages, 2000.

Chou, Hou-Pu et al., "Multiple Disease Diagnostics On A Single Chip," Biophysics Lab, Caltech, pp. 1-4, Mar. 1, 2000.

Fettinger, J. C. et al., "Stacked Modules For Micro Flow Systems In Chemical Analysis: Concept And Studies Using An Enlarged Model," Sensors and Actuators B, vol. 17, pp. 19-25, 1993.

Folch, A. et al., "Molding Of Deep Polydimethylsiloxane Microstructures For Microfluidics And Biological Applications," Journal of Biomechanical Engineering, vol. 121, pp. 28-34, Feb. 1999.

Galambos, Paul et al., "Electrical And Fluidic Packaging Of Surfacae Micromachined Electro-Microfluidic Devices," 8 pages, no date.

Greene, Chana, "Characterizing The Properties Of PDMS," pp. 1-11, Summer 2000.

Guerin, L. J. et al., "Simple And Low Cost Fabrication Of Embedded Micro-Channels By Using A New Thick-Film Photoplastic," Transducers '97, 1997 International Conference on Solid-State Sensors and Actuators, Chicago, Illinois, pp. 1419-1422, Jun. 18-19, 1997.

Hicks, Jennifer, "Genetics And Drug Discovery Dominate Microarray Research," R&D Magazine, pp. 28-33, Feb. 1999.

Jo, Byung-Ho et al., "Fabrication Of Three-Dimensional Microfluidic Systems By Stacking Molded Polydimethylsiloxane (PDMS) Layers" SPIE, vol. 3877, pp. 222-229, Sep. 1999.

Jo, Byung-Ho et al., "Three-Dimensional Micro-Channel Fabrication In Polydimethylsiloxane (PDMS) Elastomer," Journal of Microelectromechanical Systems, vol. 9, No. 1, pp. 76-81. Mar. 2000.

Kagan, C. R., "Organic-Inorganic Hybrid Materials As Semiconducting Channels In Thin-Film Field-Effect Transistors," Science, vol. 286, pp. 945-947, Oct. 29, 1999.

Kapur, Ravi et al., "Fabrication And Selective Surface Modification Of 3-Dimensionally Textured Biomedical Polymers From Etched Silicon Substrates," Journal of Biomedical Materials Research, vol. 33, pp. 205-216, 1996.

Khoo, Melvin et al., "A Novel Micromachined Magnetic Membrane Microfluid Pump," pp. 1-4, no date.

Kim, Enoch et al., "Polymer Microstructures Formed By Moulding In Capillaries," Nature, vol. 376, pp. 581-584, Aug. 17, 1995.

Kirk-Othmer, "Concise Encyclopedia of Chemical Technology," John Wiley & Sons, 5 pages, no date.

Kumar, Amit et al., "Features Of Gold Having Micrometer To Centimeter Dimensions Can Be Formed Through A Combination Of Stamping With An Elastomeric Stamp And An Alkanethiol 'Ink' Followed By Chemical Etching," Appl. Phys. Lett., vol. 63, No. 14, pp. 2002-2004, Oct. 4, 1993.

Kumar, Amit et al., "Patterning Self-Assembled Monolayers: Applications In Materials Science," Langmuir, vol. 10, pp. 1498-1511, 1994.

Lagally, Eric T. et al., "Monolithic Integrated Microfluidic DNA Amplification And Capillary Electrophoresis Analysis System," Sensors and Actuators B, vol. 63, pp. 138-146, 2000.

Lammerink, T. S. J. et al., "Modular Concept For Fluid Handling Systems," IEEE, pp. 389-394, 1996.

Li, Paul C. H. et al., "Transport, Manipulation, And Reaction Of Biological Cells On-Chip Using Electrokinetic Effects," Analytical Chemistry, vol. 69, No. 8, pp. 1564-1568, Apr. 15, 1997.

Licklider, Larry et al., "A Micromachined Chip-Based Electrospray Source For Mass Spectrometry," Analytical Chemistry, vol. 72, No. 2, pp. 367-375, Jan. 15, 2000.

Manz, A. et al., "Micromachining Of Monocrystalline Silicon And Glass For Chemical Analysis Systems," Trends in Analytical Chemistry, vol. 10, No. 5, pp. 144-149, 1991.

Marshall, Sid, "Fundamental Changes Ahead For Lab Instrumentation," R&D Magazine, 5 pages, Feb. 1999.

Marsili, Ray, "Lab-On-A-Chip Poised To Revolutionize Sample Prep," R&D Magazine, 5 pages, Feb. 1999.

McDonald, J. Cooper et al., "Fabrication Of Microfluidic Systems In Poly(dimethylsiloxane)," Electrophoresis, vol. 21, pp. 27-40, 2000.

Oleschuk, Richard D. et al., "Analytical Microdevices For Mass Spectrometry," Trends In Analytical Chemistry, vol. 19, No. 6, pp. 379-388, 2000.

Sanjoh, Akira et al., "Spatiotemporal Protein Crystal Growth Studies Using Microfluidic Silicon Devices," Journal of Crystal Growth, vol. 196, pp. 691-702, 1999.

Thompson, L. F. et al., "Introduction To Microlithography," 185th Meeting of the American Chemical Society, Seattle, WA, pp. 2 cover pages, 1-13, Mar. 20-25, 1983.

Van den Berg, A. et al., "Micro Total Analysis Systems," Proceedings of the µTAS '94 Workshop, University of Twente, The Netherlands, 17 pages, Nov. 21-22, 1994.

Verpoorte, Elisabeth M. J. et al., "Three-Dimensional Micro Flow Manifolds For Miniaturized Chemical Analysis Systems," J. Micromech. Microeng., vol. 7, pp. 246-256, 1994.

Wilbur, James L. et al., "Lithographic Molding: A Convenient Route To Structures With Sub-Micrometer Dimensions," Adv. Mater., vol. 7, No. 7, pp. 649-652, 1995.

Xia, Younan et al., "Reduction In The Size Of Features Of Patterned SAMs Generated By Microcontact Printing With Mechanical Compression Of The Stamp," Adv. Mater., vol. 7, No. 5, pp. 471-473, 1995.

Xu, Bing et al., "Making Negative Poisson's Ratio Microstructures By Soft Lithography," Adv. Mater., vol. 11, No. 14, pp. 1186-1189, 1999.

Yang, Xing et al., "A Low Power MEMS Silicone/Parylene Valve," Solid-State Sensor and Actuator Workshop, Hilton Head Island, South Carolina, 4 pages, Jun. 7-11, 1998.

"Last Chance For Micromachines," The Economist Technology Quarterly, 8 pages, Dec. 7, 2000.

Black, Harvey, "Tiny Technology Promises Tremendous Profits," The Scientist, vol. 15, No. 21, 4 pages. Oct. 29, 2001.

Calkins, Kathryn, "Mycometrix: Rubber Chips," BioCentury, 2 pages, Oct. 16, 2000.

Chou, Hou-Pu et al., "A Microfabricated Rotary Pump," Biomedical Microdevices, vol. 3, No. 4, pp. 323-330, 2001.

Eyal, Shulamit et al., "Velocity-Independent Microfluidic Flow Cytometry," Electrophoresis, vol. 23, pp. 2653-2657, 2002.

Fitzgerald, Deborah A., "Making Every Nanoliter Count," The Scientist, vol. 15, No. 21, 8 pages, Oct. 29, 2001.

Gao, Jun et al., "Integrated Microfluidic System Enabling Protein Digestion, Peptide Separation, And Protein Identification," Analytical Chemistry, vol. 73, No. 11, pp. 2648-2655, Jun. 1, 2001.

Garno, Jayne C. et al., "Production Of Periodic Arrays Of Protein Nanostructures Using Particle Lithography," Langmuir, vol. 18, No. 21, pp. 8186-8192, 2002.

Hofmann, Oliver et al., "Modular Approach To Fabrication Of Three-Dimensional Microchannel Systems in PDMS—Application to Sheath Flow Microchips," Lab on a Chip, vol. 1, pp. 108-114, 2001.

Horn, Howard, "Lab Chips Sector: Microtechologies Are Changing Healthcare And More," Life Sciences, pp. 19-21, Mar. 20, 2001.

Lagally, Eric T. et al., "Fully Integrated PCR-Capillary Electrophoresis Microsystem For DNA Analysis," Lab On A Chip, vol. 1, pp. 102-107, 2001.

Lagally, E. T. et al., "Single-Molecule DNA Amplification And Analysis In An Integrated Microfluidic Device," Analytical Chemistry, vol. 73, No. 3, pp. 565-570, Feb. 1, 2001.

Liu, Jian et al., "A Nanoliter Rotary Device For Polymerase Chain Reaction," Electrophoresis, vol. 23, pp. 1531-1536, 2002.

McDonald, J. Cooper et al., "Poly(dimethylsiloxane) As A Material For Fabricating Microfluidic Devices," Accounts of Chemical Research, vol. 35, No. 7, pp. 491-499, 2002.

Ng, Jessamine M. K. et al., "Components For Integrated Poly(Dimethylsiloxane) Microfluidic Systems," Electrophoresis, vol. 23, pp. 3461-3473, 2002.

Sherlin, Luke D. et al., "Chemical And Enzymatic Synthesis Of tRNAs For High-Throughput Crystallization," RNA, vol. 7, pp. 1671-1678, 2001.

Thorsen, Todd et al., "Dynamic Pattern Formation In A Vesicle-Generating Microfluidic Device," Physical Review Letters, vol. 86, No. 18, pp. 4163-4166, Apr. 30, 2001.

Van der Woerd, Mark et al., "Lab-On-A-Chip Based Protein Crystallization," National Aeronautics and Space Administration and Caliper, pp. 1-27, Oct. 25, 2001.

Whitesides, George M. et al., "Flexible Methods For Microfluidics," Physics Today, pp. 42-48, Jun. 2001.

Whitesides, George M. et al., "Soft Lithography In Biology And Biochemistry," Annu. Rev. Biomed. Eng., vol. 3, pp. 335-373, 2001.

Zhao, Zhan, et al., "An Integrated Biochip Design And Fabrication," Proceedings of SPIE, vol. 4936, pp. 321-326, 2002.

* cited by examiner

Sheath fluid is injected via a wider channel ABOVE the reagent injection channel.

The two angled arms are not shown, but they inject sheath fluid at this point, from the side.

| AAA | ACA | AGA | ATA | AAA | ACA | AGA | ATA | AAA | ACA | AGA | ATA | AAA | ACA | AGA | ATA |
|-----|-----|-----|-----|-----|-----|-----|-----|-----|-----|-----|-----|-----|-----|-----|-----|
| CAA | CCA | CGA | CTA | CAA | CCA | CGA | CTA | CAA | CCA | CGA | CTA | CAA | CCA | CGA | CTA |
| GAA | GCA | GGA | GTA | GAA | GCA | GGA | GTA | GAA | GCA | GGA | GTA | GAA | GCA | GGA | GTA |
| TAA | TCA | TGA | TTA | TAA | TCA | TGA | TTA | TAA | TCA | TGA | TTA | TAA | TCA | TGA | TTA |
| AAC | ACC | AGC | ATC | AAC | ACC | AGC | ATC | AAC | ACC | AGC | ATC | AAC | ACC | AGC | ATC |
| CAC | CCC | CGC | CTC | CAC | CCC | CGC | CTC | CAC | CCC | CGC | CTC | CAC | CCC | CGC | CTC |
| GAC | GCC | GGC | GTC | GAC | GCC | GGC | GTC | GAC | GCC | GGC | GTC | GAC | GCC | GGC | GTC |
| TAC | TCC | TGC | TTC | TAC | TCC | TGC | TTC | TAC | TCC | TGC | TTC | TAC | TCC | TGC | TTC |
| AAG | ACG | AGG | ATG | AAG | ACG | AGG | ATG | AAG | ACG | AGG | ATG | AAG | ACG | AGG | ATG |
| CAG | CCG | CGG | CTG | CAG | CCG | CGG | CTG | CAG | CCG | CGG | CTG | CAG | CCG | CGG | CTG |
| GAG | GCG | GGG | GTG | GAG | GCG | GGG | GTG | GAG | GCG | GGG | GTG | GAG | GCG | GGG | GTG |
| TAG | TCG | TGG | TTG | TAG | TCG | TGG | TTG | TAG | TCG | TGG | TTG | TAG | TCG | TGG | TTG |
| AAT | ACT | AGT | ATT | AAT | ACT | AGT | ATT | AAT | ACT | AGT | ATT | AAT | ACT | AGT | ATT |
| CAT | CCT | CGT | CTT | CAT | CCT | CGT | CTT | CAT | CCT | CGT | CTT | CAT | CCT | CGT | CTT |
| GAT | GCT | GGT | GTT | GAT | GCT | GGT | GTT | GAT | GCT | GGT | GTT | GAT | GCT | GGT | GTT |
| TAT | TCT | TGT | TTT | TAT | TCT | TGT | TTT | TAT | TCT | TGT | TTT | TAT | TCT | TGT | TTT |

FIG. 13C

| AAAA | ACAA | AGAA | ATAA | AAAC | ACAC | AGAC | ATAC | AAAG | ACAG | AGAG | ATAG | AAAT | ACAT | AGAT | ATAT |
|---|---|---|---|---|---|---|---|---|---|---|---|---|---|---|---|
| CAAA | CCAA | CGAA | CTAA | CAAC | CCAC | CGAC | CTAC | CAAG | CCAG | CGAG | CTAG | CAAT | CCAT | CGAT | CTAT |
| GAAA | GCAA | GGAA | GTAA | GAAC | GCAC | GGAC | GTAC | GAAG | GCAG | GGAG | GTAG | GAAT | GCAT | GGAT | GTAT |
| TAAA | TCAA | TGAA | TTAA | TAAC | TCAC | TGAC | TTAC | TAAG | TCAG | TGAG | TTAG | TAAT | TCAT | TGAT | TTAT |
| AACA | ACCA | AGCA | ATCA | AACC | ACCC | AGCC | ATCC | AACG | ACCG | AGCG | ATCG | AACT | ACCT | AGCT | ATCT |
| CACA | CCCA | CGCA | CTCA | CACC | CCCC | CGCC | CTCC | CACG | CCCG | CGCG | CTCG | CACT | CCCT | CGCT | CTCT |
| GACA | GCCA | GGCA | GTCA | GACC | GCCC | GGCC | GTCC | GACG | GCCG | GGCG | GTCG | GACT | GCCT | GGCT | GTCT |
| TACA | TCCA | TGCA | TTCA | TACC | TCCC | TGCC | TTCC | TACG | TCCG | TGCG | TTCG | TACT | TCCT | TGCT | TTCT |
| AAGA | ACGA | AGGA | ATGA | AAGC | ACGC | AGGC | ATGC | AAGG | ACGG | AGGG | ATGG | AAGT | ACGT | AGGT | ATGT |
| CAGA | CCGA | CGGA | CTGA | CAGC | CCGC | CGGC | CTGC | CAGG | CCGG | CGGG | CTGG | CAGT | CCGT | CGGT | CTGT |
| GAGA | GCGA | GGGA | GTGA | GAGC | GCGC | GGGC | GTGC | GAGG | GCGG | GGGG | GTGG | GAGT | GCGT | GGGT | GTGT |
| TAGA | TCGA | TGGA | TTGA | TAGC | TCGC | TGGC | TTGC | TAGG | TCGG | TGGG | TTGG | TAGT | TCGT | TGGT | TTGT |
| AATA | ACTA | AGTA | ATTA | AATC | ACTC | AGTC | ATTC | AATG | ACTG | AGTG | ATTG | AATT | ACTT | AGTT | ATTT |
| CATA | CCTA | CGTA | CTTA | CATC | CCTC | CGTC | CTTC | CATG | CCTG | CGTG | CTTG | CATT | CCTT | CGTT | CTTT |
| GATA | GCTA | GGTA | GTTA | GATC | GCTC | GGTC | GTTC | GATG | GCTG | GGTG | GTTG | GATT | GCTT | GGTT | GTTT |
| TATA | TCTA | TGTA | TTTA | TATC | TCTC | TGTC | TTTC | TATG | TCTG | TGTG | TTTG | TATT | TCTT | TGTT | TTTT |

COMBINATORIAL SYNTHESIS SYSTEM

CROSS-REFERENCES TO RELATED APPLICATIONS

This application is a Continuation-In-Part Application of U.S. patent application Ser. No. 09/679,432, filed Oct. 3, 2000 now U.S. Pat. No. 6,508,988, which is incorporated herein by reference in its entirety.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. HG-01642-02, awarded by the National Institutes of Health.

FIELD OF THE INVENTION

The present invention relates to a chemical reaction apparatus for synthesizing an array of compounds. In particular, the present invention relates to a microfluidic chemical reaction apparatus for a combinatorial synthesis.

BACKGROUND OF THE INVENTION

Methods for synthesizing polymers (e.g., oligonucleotides) on a solid support have been developed for producing large arrays of polymer sequences on solid substrates. These large "arrays" of polymer sequences have wide ranging applications and are of substantial importance to many industries including, but not limited to, the pharmaceutical, biotechnology and medical industries. For example, the arrays can be used in screening large numbers of molecules for biological activity, e.g., receptor binding capability. And arrays of oligonucleotide probes can be used to identify mutations in known sequences, as well as in methods for de novo sequencing of target nucleic acids. In addition, PNA (peptide nucleic acids) arrays can be used to screen molecules which are useful in antisense (mRNA) gene regulation, or molecules which bind to specific sequences of double-stranded DNA. Furthermore, combinatorial arrays can be used in gene expression analysis. See, for example, van Dam et al., *Genome Research*, 2002, 12, 145–152, which is incorporated herein by reference in its entirety.

Oligonucleotide arrays with up to hundreds of thousands of samples on an area of a few square centimeters have been synthesized and proven to be extraordinarily useful in various applications including gene expression studies. Over the past several years, a new set of technologies have emerged for making arrays of synthetic surface-bound polymers.

One method for synthesizing high-density patterns on surfaces is photolithography process as discussed in U.S. Pat. No. 5,143,854, issued to Pirrung et al., and PCT Application No. 92/10092. In this method, light is directed to selected regions of a substrate to remove protecting groups from the selected regions of the substrate. Thereafter, selected molecules are coupled to the substrate, followed by additional irradiation and coupling steps. By activating selected regions of the substrate and coupling selected monomers in precise order, one can synthesize an array of molecules having any number of different sequences, where each different sequence is in a distinct, known location on the surface of the substrate. This method requires specialized reagents (e.g., photoremovable protecting groups), which is relatively expensive and presently have significantly lower coupling yield than conventional reagents. Moreover, in general, to make an array of N-mers requires 4N cycles of deprotection and coupling, one for each of the 4 bases, times N base positions. This photolithographic method also typically requires 4N masks, thereby adding a considerable expense to the procedure. Furthermore, any decreased deprotection efficiency results in the decreased coupling efficiency. And because the deprotection reaction generally does not result in 100% cleavage of the protecting groups, there can be "deletion sequences." For example, if one strand is accidentally not deprotected, but becomes deprotected later, then it will have missed one or more coupling steps. Conventional reagents do not suffer this problem because it is the coupling step which is most inefficient, and missed couplings can be terminated (nearly completely) with the capping step. Thus with conventional reagents, impurities consist of truncated sequences, but with photocleavable reagents, impurities consist of truncated and deletion sequences.

Another method for producing polymer arrays is an ink-jet technique which uses the print heads of commercial piezoelectric ink-jet printers to deliver reagents to individual spots on the array. While this technique uses relatively inexpensive conventional chemical reagents with typically high coupling yield, it can deliver one, and only one, drop of reagents at a time, unless multiple jets are used simultaneously. Moreover, the solid support must be patterned to achieve small feature sizes. Furthermore, two drops of liquid applied too closely together on a surface tend to spread into each other and mix, thereby limiting the array density achievable with the ink-jet method.

There are other methods including robotic deposition of reagents in an array of fluid-containing wells and the use of fluidics to deposit reagents on a surface. See for example, U.S. Pat. No. 6,001,311, issued to Brennan et al. and U.S. Pat. No. 6,121,048, issued to Zaffaroni et al. However, each method has its own limitations such as limited array density, increased production cost per array, and/or serial (i.e., non-parallel) synthesis.

Therefore, there is a need for a chemical reaction apparatus and a method for preparing array of compounds with high throughput, high product quality, enhanced miniaturization and lower costs.

SUMMARY OF THE INVENTION

The present invention provides a microfluidic combinatorial chemical synthesis device and a method for using the same. The microfluidic device of the present invention comprises:

a plurality of microfluidic flow channels defined by an elastomeric layer and a solid support, wherein flow channels are adapted to allow flow of a solution therethrough, and wherein the solid support comprises a reactive functional group within an inner surface of the flow channels for attaching a reactive reagent thereto;

a plurality of control channels; and a plurality of valves disposed in between said fluid flow channel and said control channel to regulate flow of the solution through said fluid flow channels, wherein each of said valves comprises one of said control channels and a segment of said elastomeric layer that is deflectable into or retractable from said fluid flow channel upon which said valve operates in response to an actuation force applied to said control channel, said elastomeric segment when positioned in said flow channel restricting solution flow therethrough.

In one embodiment of the present invention, the inner surface of the flow channels comprising the elastomeric layer is coated with a coating material that is substantially inert to the chemical reaction solvent. In one particular embodiment, the coating material is selected from the group consisting of a fluoropolymer, Vitrinite® protective coating, and silicon dioxide.

In another embodiment, the microfluidic device comprises a thin layer of an elastomeric material disposed in between a solid support flow channel layer and a control channel layer. The solid support is, preferably, selected from the group consisting of glass, polystyrene, polystyrene-divinylbenzene copolymer, silicone rubber, quartz, latex, polyurethane, a derivatizable transition metal, silicon dioxide, silicon nitride, gallium arsenide, and a derivative thereof. Preferably, the derivatizable transition metal is gold. The control layer can also be a solid support described above or any other suitable material, including rigid and elastomeric polymer.

In yet another embodiment, both the fluid flow layer and the control channel layer are solid supports made of a rigid material, such that the fluid flow channels and/or the control channels comprise a channel within the rigid materials. In one particular embodiment, the elastomeric layer is disposed, preferably removeably, in between the rigid materials, such that the fluid flow channels and the control channels are formed within the interfaces of the rigid materials and the elastomeric material.

Still in another embodiment, at least a portion of the control channels are aligned in between the fluid flow channels. In addition, at least a portion of the control channels is aligned on top of the fluid flow channels. In this manner, actuation of the control channel controls the fluid flow within the fluid flow channels that are positioned directly below the control channels.

In another embodiment, the control channels are aligned on top of the fluid flow channels. In this embodiment, the control channels comprise a narrow cross-section area and a wide cross-section area within each control channels, such that when the control channel is actuated, only the valves comprising the wide cross-section area restrict fluid flow.

Another aspect of the present invention provides a method for synthesizing a library of compound on a microfluidic device comprising (i) a plurality of fluid flow channels defined by an elastomeric layer and a solid support, where in the flow channels are adapted to allow the flow of a solution therethrough, and wherein the solid support comprises a reactive functional group with the inner surface of the flow channels for attaching a reactive reagent thereto; (ii) a means for rendering the elastomeric layer of the inner surface of the flow channels substantially inert to a chemical reaction solvent; (iii) a plurality of control channels; and (iv) a plurality of valves disposed in between the fluid flow channel and the control channel to regulate flow of the solution through the fluid flow channels, wherein each of the valves comprises one of the control channels and a segment of the elastomeric layer that is deflectable into or retractable from the fluid flow channel upon which the valve operates in response to an actuation force applied to the control channel, the elastomeric segment when positioned in the flow channel restricting solution flow therethrough. The method comprises:

(a) producing a solid-support bound compound by introducing a first reactive reagent into the fluid flow channels under conditions sufficient to covalently attach at least a portion of the first reactive reagent to the reactive functional group of the inner surface of the fluid flow channel;

(b) modifying the solid support-bound compound by introducing another reactive reagent into the fluid flow channels under conditions sufficient to react the solid-support bound compound with the reactive reagent; and (c) optionally repeating said step (b).

In one embodiment, different reactive reagents are added to different flow channels in the step (a) or (b) or both. Preferably, a homogeneous reagent is added to each of the flow channels.

The method can further comprise cleaving the library of solid-support bound compounds from the inner surface of the microfluidic device.

In one particular embodiment, the means for rendering the elastomeric layer of the inner surface of the flow channels substantially inert to a chemical reaction solvent comprises a coating material that is substantially inert to the chemical reaction solvent. Preferably, the coating material is selected from the group consisting of a fluoropolymer, Vitrinite® protective coating, and silicon dioxide.

In another embodiment, the means for rendering the elastomeric layer of the inner surface of the flow channels substantially inert to a chemical reaction solvent comprises providing a laminar flow of a sheath fluid in between the chemical reaction mixture and the elastomeric layer portion of the inner surface. The sheath fluid is selected such that it is compatible with the chemical reaction solvent and the inner surface. Thus, the sheath fluid serves as at least a partial barrier between the elastomeric layer and the reactive reagent.

Yet, in another embodiment, the microfluidic device comprises an elastomeric layer and a solid support base. In this embodiment, the fluid flow channel is, preferably, located on the interface of the elastomeric layer and the solid support base. When the elastomeric layer is removeably attached to the solid support base, prior to said step (b) of introducing another reagent, the method can further comprise:

(A) removing the elastic layer from the solid support; and (B) reattaching the elastic layer to the solid support at a different angle, such that the newly formed flow channels intersect the flow channels of the microfluidic device of said step (a).

In another embodiment, the plurality of flow channels comprises a first set of flow channels and a second set of flow channels such that the first set of flow channels intersect the second set of flow channels, thus resulting in a plurality of flow channel intersections. In this manner, the reactive reagent in said step (a) can be introduced into the first set of flow channels and the reactive reagent in said step (b) can be introduced into the second set of flow channels.

BRIEF DESCRIPTION OF THE DRAWINGS

FIGS. 13A–D are illustrations of respective nucleotides added to the microfluidic combinatorial chemical synthesis device of the present invention after each step in Example 2.

DETAILED DESCRIPTION OF THE INVENTION

I. Definitions

Figure 1A:
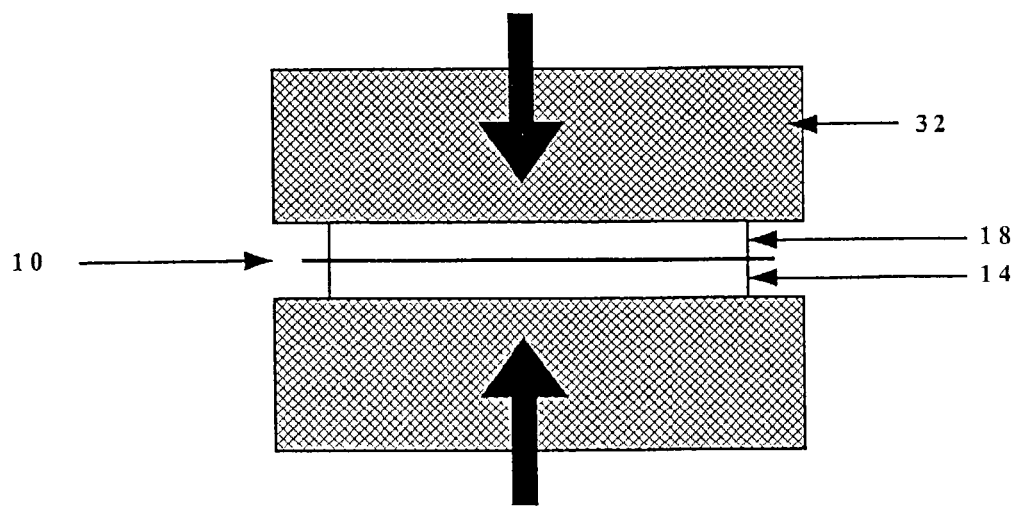
FIG. 1A is a schematic illustration of a microfluidic device comprising an elastomeric layer sandwiched in between two rigid solid support, in which the device is held together mechanically.

The term "channel" refers to an enclosed passage (e.g., conduit) within a microfluidic device through which a fluid can flow. The channel can have one or more openings for introduction of a fluid. Typically, the channel is formed by sandwiching two or more materials (e.g., an elastomeric polymer and a solid support), where at least one of the material comprises a groove (e.g., depressions) within its surface. This grooved surface is attached to another material which encloses the groove and forms a channel. Alternatively, two grooved surfaces, each forming a portion of the channel, can be attached together such that the two grooved surfaces when combined form a complete channel.

"Fluid" refers to a gas or liquid. Preferably, fluid is a liquid.

The term "valve" unless otherwise indicated refers to a configuration in which a fluid flow channel (i.e., flow channel) and a control channel intersect and are separated by an elastomeric segment that can be deflected into or retracted from the flow channel in response to an actuation force.

The term "elastomer" and "elastomeric" has its general meaning as used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials can be characterized by a Young's modulus. The elastomeric materials utilized in the microfluidic devices disclosed herein typically have a Young's modulus of between about 1 Pa–1 TPa, in other instances between about 10 Pa–100 GPa, in still other instances between about 20 Pa–1 GPa, in yet other instances between about 50 Pa–10 MPa, and in certain instances between about 100 Pa–1 MPa. Elastomeric materials having a Young's modulus outside of these ranges can also be utilized depending upon the needs of a particular application.

The term "integrated elastomer structure" or "integrated elastomer device" refers to one or more elastomer layers which have been permanently bonded together to form a microfluidic device.

The term "top-aligned control channel" or "above-aligned control channel" refers to a control channel which is in the same direction as the fluid flow channel and which is situated on top of the fluid flow channel when viewed from the top surface of the microfluidic device.

The term "adjacent control channel" refers to a control channel which is in the same direction as the fluid flow channel and which is situated adjacent to the fluid flow channel or in between two fluid flow channels when viewed from the top of the microfluidic device.

"Combinatorial library" or "array of compounds" refers to a preselected collection of different compounds, polymer sequences or probes which are associated with a surface of a solid support base. An array may include polymers of a given length having all possible monomer sequences made up of a specific basis set of monomers, or a specific subset of such an array. For example, an array of all possible oligonucleotides of length 8 includes 65,536 different sequences. However, an array may include only a subset of the complete set of monomers. Similarly, a given array may exist on more than one separate solid support base, e.g., where the number of sequences necessitates a larger surface area in order to include all of the desired polymer sequences.

The term "monomer", "reactive reagent" and "building block" are used interchangeably herein and refer to a member of the set of smaller molecules which can be joined together to form a larger molecule or polymer. Exemplary monomers include, but are not limited to, natural or synthetic amino acids (including common L-amino acids and D-amino acids), nucleotides (including PNA, and natural and unnatural ribonucleotides and deoxyribonucleotides) and polysaccharides (including pentoses and hexoses). As used herein, monomer refers to any member of a basis set for synthesis of a larger molecule. A selected set of monomers forms a basis set of monomers. For example, the basis set of nucleotides includes A, T (or U), G and C. In another example, dimers of the 20 naturally occurring L-amino acids form a basis set of 400 monomers for synthesis of polypeptides. Different basis sets of monomers may be used in any of the successive steps in the synthesis of a polymer. Furthermore, each of the sets may include protected members which are modified after synthesis. It should be appreciated that the monomer units, while not necessary, are often protected in such a way that only one monomer unit is added at a time. When the monomer units contain a protecting group, a deblocking reaction is then needed to remove the protecting group before adding the next monomer unit, for example, in non-array DNA and peptide synthesis.

"Homogeneous reagent" or "homogeneous monomer" refers to a reaction mixture having one monomer.

"Heterogeneous reagent" or "heterogeneous monomer" refers to a reaction mixture having a mixture of different monomers.

The present invention provides microfluidic chemical reaction devices, which are particularly useful in a combinatorial synthesis. Because microfluidic devices of the present invention require only a small amount of reagents, they are particularly suited for a small scale combinatorial synthesis. Methods of fabricating microfluidic devices of the present invention are generally discussed in the commonly assigned U.S. patent application Ser. No. 09/605,520, filed on Jun. 27, 2000, which is incorporated herein by reference in its entirety. However, other suitable methods of fabricating microfluidic devices, including modifying the methods disclosed in the above incorporated U.S. patent application Ser. No. 09/605,520, are also contemplated to be within the scope of the present invention.

Some of the microfluidic devices described herein are fabricated from, or comprise, an elastomeric polymer such as Coming Sylgard 184, GE RTV 615 (formulation), and other a vinyl-silane crosslinked (type) silicone elastomer (family). However, the present microfluidic devices are not limited to this formulation, type or even this family of polymer; rather, nearly any polymer, preferably elastomeric polymer, is suitable. Given the tremendous diversity of polymer chemistries, precursors, synthetic methods, reaction conditions, and potential additives, there are a large number of possible elastomer systems that can be used to make monolithic elastomeric microvalves and pumps. The choice of materials typically depends upon the particular material properties (e.g., solvent resistance, stiffness, gas permeability, and/or temperature stability) required for the application being conducted. Additional details regarding the type of elastomeric materials that can be used in the manufacture of the components of the microfluidic devices disclosed herein are set forth in U.S. patent application Ser. No. 09/605,520, and PCT Application No. 00/17740, both of which are incorporated herein by reference in their entirety.

II. Overview

A variety of microfluidic devices and methods for conducting combinatorial synthesis are provided herein. The devices in general include a microfabricated flow channel. Preferably, microfluidic devices of the present invention comprise a plurality of flow channels. In this manner, a plurality of reactions can be achieved simultaneously on a single device.

The devices can further include various other components such as control channels, valves and/or pumps, at least some of which are manufactured from elastomeric materials. This is in sharp contrast to conventional microfluidic devices that typically are based on silicon substrates (i.e., silicon chips). Still other microfluidic devices provided herein comprise a plurality of intersecting flow channels to form an array of reaction chambers or junctions at which combinatorial synthesis can occur. As alluded to above, such devices permit a large number of reactions to be performed simultaneously thereby providing a high throughput combinatorial synthesis.

III. General Device Structure

The microfluidic devices disclosed herein are typically constructed at least in part from elastomeric materials and constructed by single and multilayer soft lithography (MLSL) techniques and/or sacrificial-layer encapsulation methods. See, for example, Unger et al. (2000) Science 288:113–116, and PCT Publication WO 01/01025, both of which are incorporated by reference herein in their entirety. Utilizing such methods, microfluidic devices can be designed in which reagent flow through flow channels of the device is controlled, at least in part, with one or more control channels that are separated from the flow channel by an elastomeric segment. This segment can be deflected into or retracted from the flow channel with which a control channel is associated by applying an actuation force to the control channels. By controlling the degree to which the segment is deflected into or retracted out from the flow channel, one can slow or entirely block solution flow through the flow channel. Using combinations of control and flow channels of this type, one can prepare a variety of different types of valves and pumps for regulating solution flow.

In one aspect of the present invention, microfluidic devices also comprise a solid support which comprises a functional group (i.e., reactive site), which allows solid support-bound combinatorial synthesis. Microfluidic devices of the present invention can be made from a single material, e.g., the solid support is also an elastomeric polymer. Preferably, however, microfluidic devices of the present invention comprise an elastomeric polymer and a solid support which is composed of a different material than the elastomeric polymer. As stated above, the solid support comprises reactive sites to allow a solid support-bound combinatorial synthesis to occur.

Some elastomeric polymers also contain functional groups which may react with the reagent that is introduced into the flow channel. To minimize or avoid this undesired reaction, in one embodiment of the present invention, a means for rendering the elastomeric polymer inert to the reaction solution is also provided. In one specific embodiment, the elastomeric polymer potion of the flow channel is coated with an inert coating. As expected, suitable inert coating depends on particular reagents used in the combinatorial synthesis. For example, in oligonucleotide synthesis, suitable inert coatings include a fluoropolymer, Vitrinite® protective coating (Tefla America, Inc., Corona, Calif.), and silicon dioxide.

In one embodiment, the devices and methods described herein utilize such valves and pumps to control reagent flow through flow channels. However, it should be appreciated other methods for affecting reagent flow through flow channels are also contemplated to be within the scope of the present invention.

As noted above, reagent flow through the flow channel is controlled using one or more control channels that are separated from the flow channel by an elastomeric segment. The deflection of such segment into the flow channel can be used to restrict of block reagent flow (i.e., as a valve) and to expel solution from one region of the flow channel to another region (i.e., as a pump). In addition, a peristaltic pumping action can be produced by staggering the time at which a series of control channels are actuated. With the use of such arrangements, one can regulate reagent flow through the flow channel without having to utilize electric fields to effectuate reagent transport, although such techniques can also be utilized in certain applications.

Thus, in operation, certain methods involve introducing a reagent into the flow channel and then actuating control channels associated with the flow channel to move the reagent from one region to another. With certain devices, reagents can be transported semi-continuously or continuously.

In addition to pressure based actuation systems described above, other methods of control channel actuation known to one skilled in the art of microfluidic devices, such as electrolytic, electrokinetic, electrostatic, and magnetic actuation systems are also contemplated to be within the scope of this invention.

The following sections describe in greater detail specific exemplary configurations that can be utilized to achieve combinatorial synthesis. It should be understood, however, that these configurations are exemplary and that modifications of these systems will be apparent to those skilled in the art.

IV. Fabrication of Microfluidic Devices

The microfluidic devices disclosed herein are typically constructed by single and multilayer soft lithography (MLSL) techniques and/or sacrificial-layer encapsulation methods. The MLSL techniques are particularly useful in some embodiments for producing microfluidic devices which comprise both the control channel and the flow channel. In general, the MLSL technique involves casting a series of elastomeric layers on a micro-machined mold, removing the layers from the mold and then fusing the layers together. In the sacrificial-layer encapsulation approach, patterns of photoresist are deposited wherever a channel is desired. The use of these techniques to fabricate elements of microfluidic devices is described, for example, by Unger et al. (2000) Science 288:113–116; by Chou, et al. (2000) "Integrated Elastomer Fluidic Lab-on-a-chip-Surface Patterning and DNA Diagnostics, in Proceedings of the Solid State Actuator and Sensor Workshop, Hilton Head, S.C.; in PCT Publication WO 01/01025; and in U.S. patent application Ser. No. 09/679,432, filed Oct. 3, 2000, all of which are incorporated herein by reference in their entirety.

More specifically, certain fabrication methods involve initially fabricating mother molds for top layers (elastomeric layer with the control channels) and bottom layers (elastomeric layer with the flow channel) on silicon wafers by photolithography with photoresist (e.g., Shipley SJR 5740). Channel heights can be controlled precisely by the spin coating rate. Photoresist channels are formed by exposing the photoresist to UV light followed by development. Heat reflow process and protection treatment is performed as described previously (M. A. Unger, H.-P. Chou, T. Throsen, A. Scherer and S. R. Quake, Science 288, 113 (2000)).

Thereafter, a mixed two-part-silicone elastomer (GE RTV 615) is spun into the bottom mold and poured onto the top mold, respectively. Again, spin coating can be utilized to control the thickness of bottom polymeric fluid layer. After baking in the oven at 80° C. for 25 minutes, the partially cured top layer is peeled off from its mold, aligned and assembled with the bottom layer. A 1.5-hour final bake at 80° C. is used to bind these two layers irreversibly. Once peeled off from the bottom silicon mother mold, this RTV device is typically treated with HCl (0.1 N, 30 min at 80° C.) to cleave some of the Si—O—Si bonds to expose hydroxy groups that make the channels more hydrophilic. The device can then be sealed hermetically to a solid support. The solid support can be manufactured of essentially any material. The surface should be flat to ensure a good seal as the seal formed is primarily due to adhesive forces. When the solid support is a rigid material additional force may be required to keep the surfaces in contact during actuation of the control channels. For example, the elastomeric layer may be mechanically held in contact with a rigid solid support.

The devices formed according to the foregoing method results in the solid support (e.g., glass slide) forming one wall of the flow channel. Such arrangements are particularly useful as the solid support provides reactive sites for conducting solid support-bound combinatorial synthesis. However, in some instances the device once removed from the mother mold is sealed to a thin elastomeric polymer such that the flow channel is totally enclosed in the elastomeric material. The resulting elastomeric device can then optionally be joined to a substrate support. Devices having this latter structure can be useful for reactions that are expected to generate or require high pressures. Such pressures can sometimes cause the seal between the elastomeric device and the substrate to fail.

It has also been found that the seal between the elastomeric structure and the solid support can be improved by cleaning the elastomeric structure, e.g., with ethanol, prior to placing the structure on the solid support. The seal between the elastomeric structure and the solid support can also be improved by pressing the elastomeric structure against the solid support.

Fluid flow through the device can be controlled by utilizing applied air pressure in the control channels. In addition, other actuation methods, such as electromagnetic and current, can also be used to control the fluid flow. In addition, other fluids could be used to actuate the control channels. For example, air is compressible, and thus experiences some finite delay between the time of application of pressure by the external activator (e.g., solenoid valve) and the time that this pressure is experienced by the membrane. In an alternative embodiment of the present invention, pressure could be applied from an external source to a noncompressible fluid such as water or hydraulic oils, resulting in a near-instantaneous transfer of this pressure to the membrane. However, if the displaced volume of the valve is large or the pressure channel is narrow, higher viscosity of a control fluid may contribute to delay in actuation. The optimal medium for transferring pressure will therefore depend upon the particular application and device configuration, and both gaseous and liquid media are contemplated by the invention.

Figures 1B, 1C:
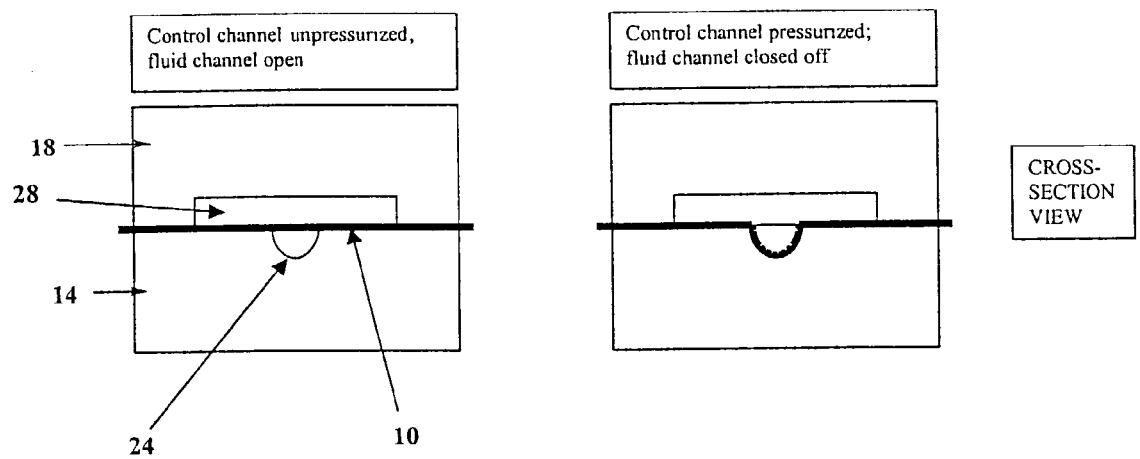
FIG. 1B is a cross-section view of the microfluidic device of FIG. 1A showing non-actuated control channel.
FIG. 1C is same view as that of FIG. 1B, wherein the control channel is actuated resulting in deflection of the elastomeric segment into the flow channel.

In another embodiment, the device does not require machining or bonding of the elastomer material. In this embodiment, as shown in FIGS. 1A–1C, a thin sheet (or layer) of the elastomer material 10, preferably a fluoroelastomer material, is disposed in between (i.e., sandwiched) two solid supports (e.g., rigid/semi-rigid flow layer and a rigid/semi-rigid control layer) 14 and 18. It should be appreciated that the control layer need not be a rigid material in this embodiment. The flow and control layers, 14 and 18, can both be made by etching channels 24 and 28 into the solid support (e.g., glass) which is inert to reaction solvents. The two solid supports 14 and 18 are aligned with the elastomer layer 10 between them, and held together with mechanical pressure (e.g., by using a clamp 32), or they can be bonded with an adhesive or other suitable means. The elastomer layer 10 acts as a seal and as valves when actuation force is applied.

In this embodiment, valve actuation is achieved because when pressure is applied to the control channel 28, the elastomeric segment deflects down into the flow channel 24. Suitable materials for elastomer layer 10 include various fluoroelastomers, such as Kalrez™, Zalak™, and Viton™ (available from Dupont and Dow). As expected, thinner elastomer layer 10 requires a less amount of actuation force. Typically, the thickness of the elastomer layer 10 is from about 0.01 to about 10 microns.

Flow Channels

Microfluidic devices of the present invention comprise a plurality of flow channels, thereby providing a means for simultaneous performing a plurality of chemical reactions at different locations within a single solid support.

In one aspect of the present invention, the elastomeric layer having a plurality of flow channels is removably attached to the solid support. In one particular embodiment, the elastomeric layer forms a reversible hermetic seal with nearly any smooth planar solid support base. An advantage to forming a seal this way is that the elastomeric layer can be peeled up (i.e., removed from the solid support), washed, re-used, and/or repositioned. This embodiment is illustrated in FIGS. 2A–2B.

Figure 2A:
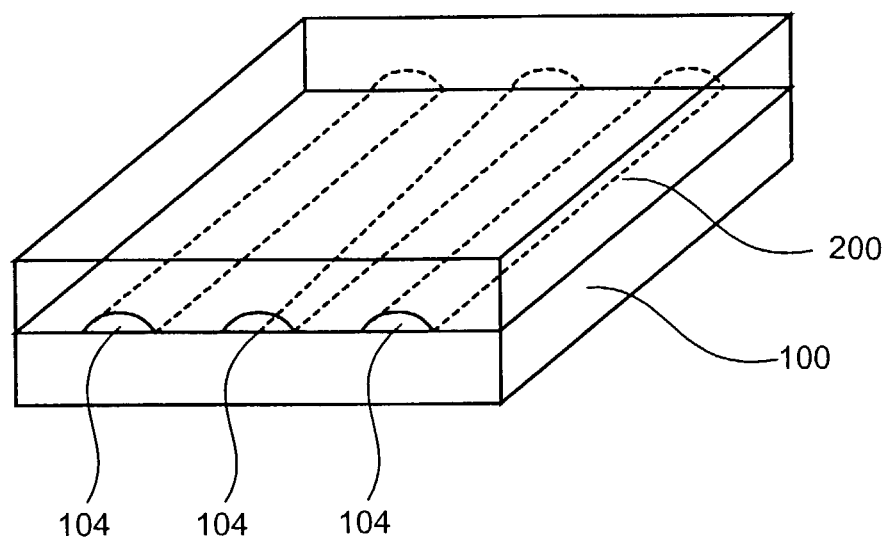
FIG. 2A depicts a single elastomeric layer microfluidic device with an illustration of the elastomeric layer positioned on top of a solid support, thereby forming a plurality of flow channels.
Figure 2B:
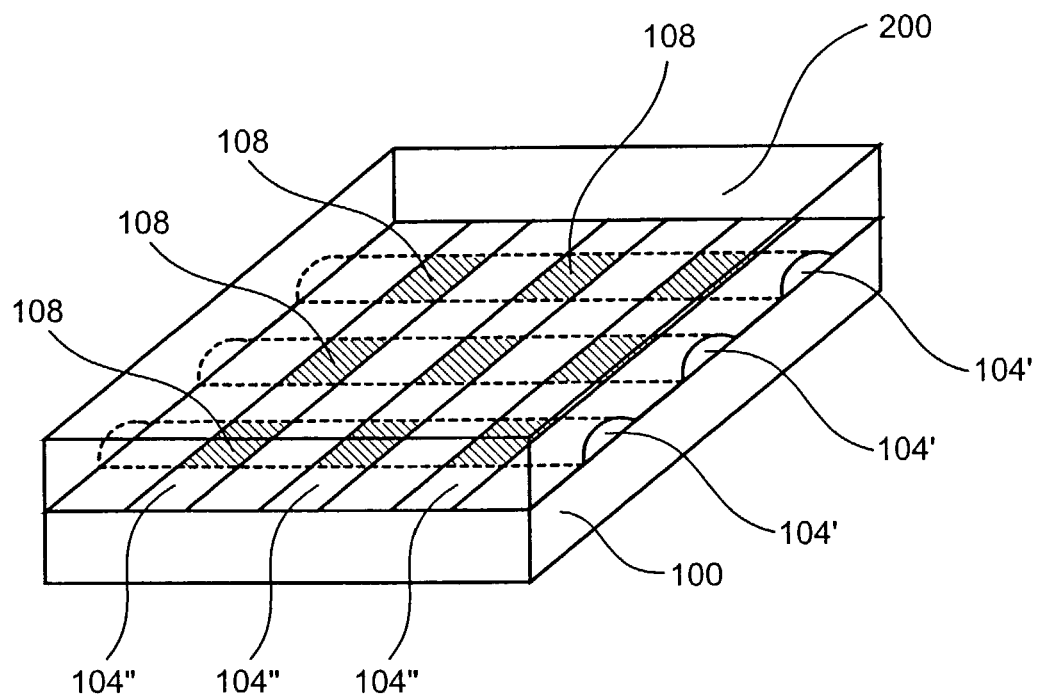
FIG. 2B is an illustration of the elastomeric layer on top of the solid support, where the elastomeric layer has been removed and repositioned on top of the solid support after 90° rotation.
Figure 4A:
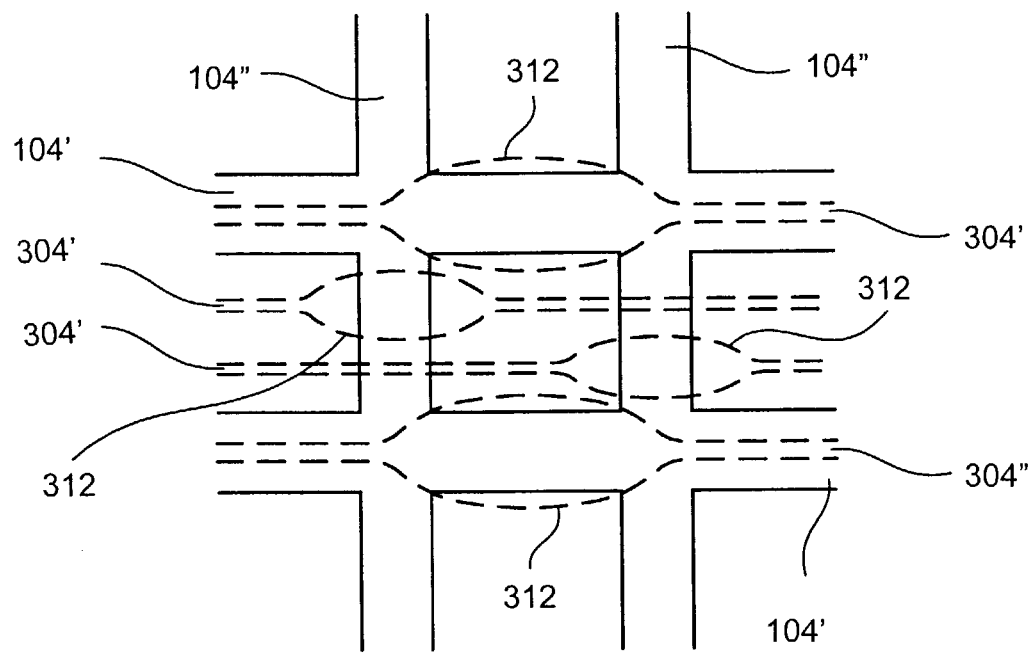
FIG. 4A is a schematic illustration of a chemical reaction apparatus having multiple control channels to permit flow control of individual flow channels.

In FIG. 2A, a first set of compounds (i.e., monomers or reactive reagents) is added to the microfluidic device through the desired plurality of flow channels 104 which is located on the interface between the elastomeric layer 200 and the solid support 100. It should be appreciated that the monomers need not be introduced to all of the flow channels 104. Monomers which are unreacted or unattached to the solid support 100 are then removed by rinsing the flow channels 104 with a solvent. Alternatively, the elastomeric layer 200 can be removed and the entire solid support 100 is rinsed with a solvent to remove unreacted monomers. The elastomeric layer 200 is removed and is reattached to the solid support 100, as shown in FIG. 2B, such that the flow channels 104' now intersect (e.g., are perpendicular to) the previous flow channels 104". Another set of monomers is then introduced into the flow channels 104' such that they react with the first monomers that are attached to the solid support 100. The reaction between the first set of monomers and the second set of monomers occurs at intersections 108. Again the excess monomers are removed. The elastomeric layer 200 is once again removed and reattached to the solid support 100 in the "original" configuration as shown in FIG. 4A. The process is repeated until a desired array of compounds is produced at the intersections 108.

To aid in alignment of the elastomeric layer 200 to the solid support 100 after each removal, an alignment guide (not shown) can be present on the elastomeric layer 200 and/or the solid support 100. The alignment guide can be as simple as marking(s) present on the elastomeric layer 200 and/or the solid support 100. Or the alignment guide can be one or more joints, e.g., having a male part on the elastomeric layer 200 and the female part on the solid support 100, or vice versa. A joint can be as simple as a combination of depression(s) and protrusion(s), which fit snugly against one another. Alternatively, the alignment guide can be a pin and hole (i.e., pin and socket) mechanism.

Figure 3:
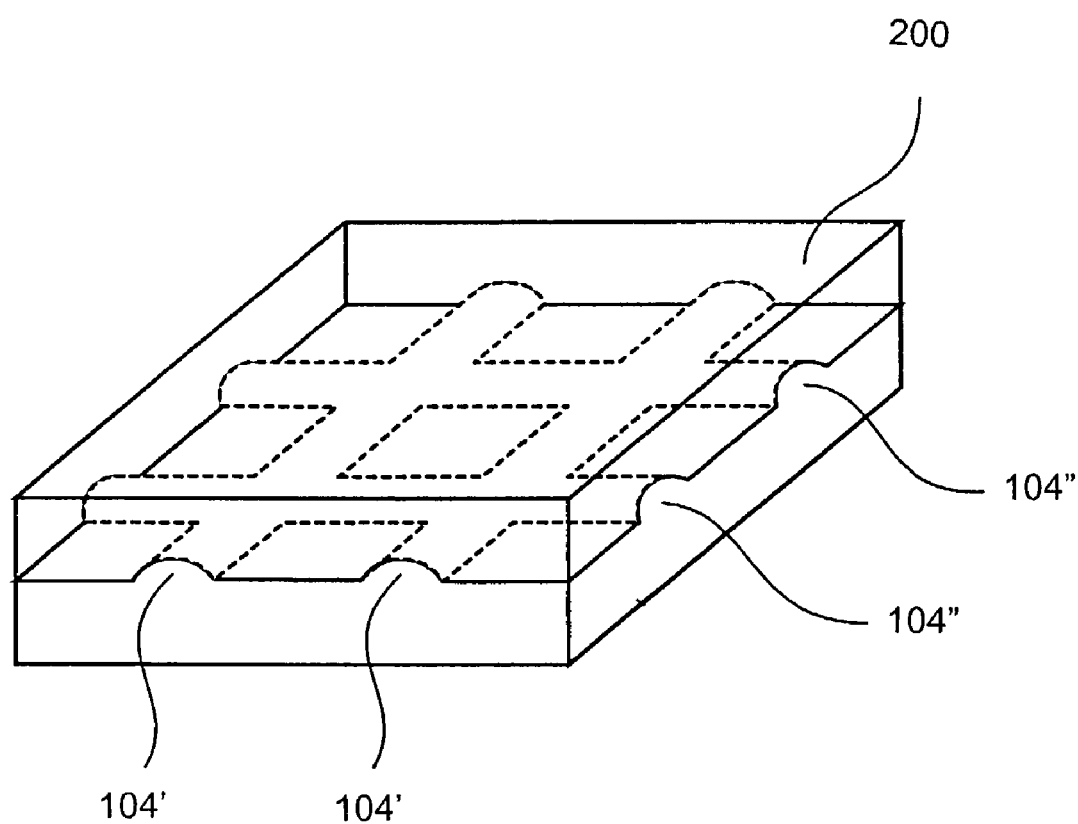
FIG. 3 is an illustration of a first elastomeric layer positioned on top of the solid support, thereby forming a plurality of flow channels.

Alternatively, microfluidic devices can be fabricated with a plurality of flow channels that intersect one another. This flow channel configuration eliminates a need for removing the elastomeric layer and reattaching it to the solid support. For example, as shown in FIG. 3, devices of this embodiment of the present invention comprise a plurality of intersecting flow channels 104' and 104". In this manner, one set of reagents is added to the flow channels 104', and another set of reagents is added to the flow channels 104". Each set of reagents is typically added separately with removal of the unreacted reagents from the flow channels prior to addition of another reagent. This addition and removal process is repeated until polymers of desired length or sequence are produced.

Control Channels

Figure 4B:
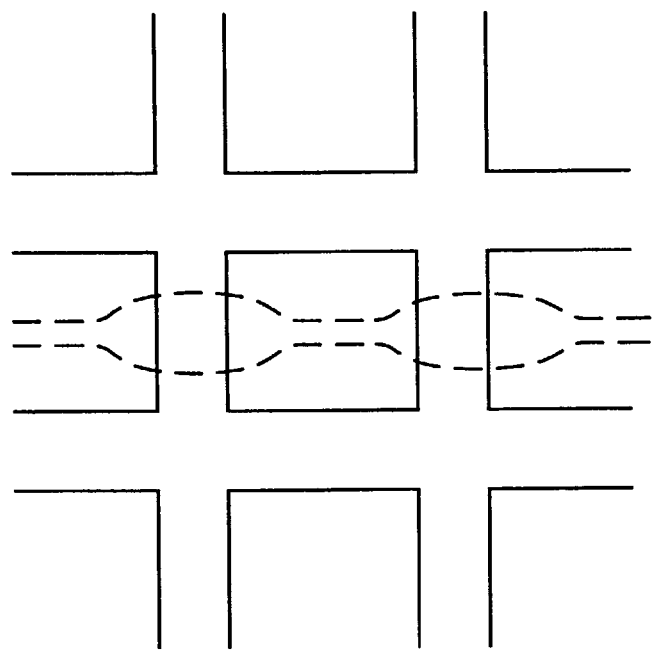
FIG. 4B is a schematic illustration of a control channel capable of controlling two flow channels simultaneously.

FIGS. 4A and 4B are schematic illustration showing flow channels (104' and 104") and control channels that are located on top of the flow channel (i.e., control channels 304") and adjacent to the flow channel (i.e., control channels 304'). The control channels are located on a plane above the flow channels and are separated by an elastomeric layer. As the Figures illustrate, the width of each of the control channels 304' and 304" vary along its axis. In this manner, when the control channel is pressurized, the large width portion(s) 312 expands and closes off the flow channel that is directly underneath the large width portion(s) of the control channel. Each of the control channels can control multiple flow channels by having more than one large width portions 312.

Figure 5:
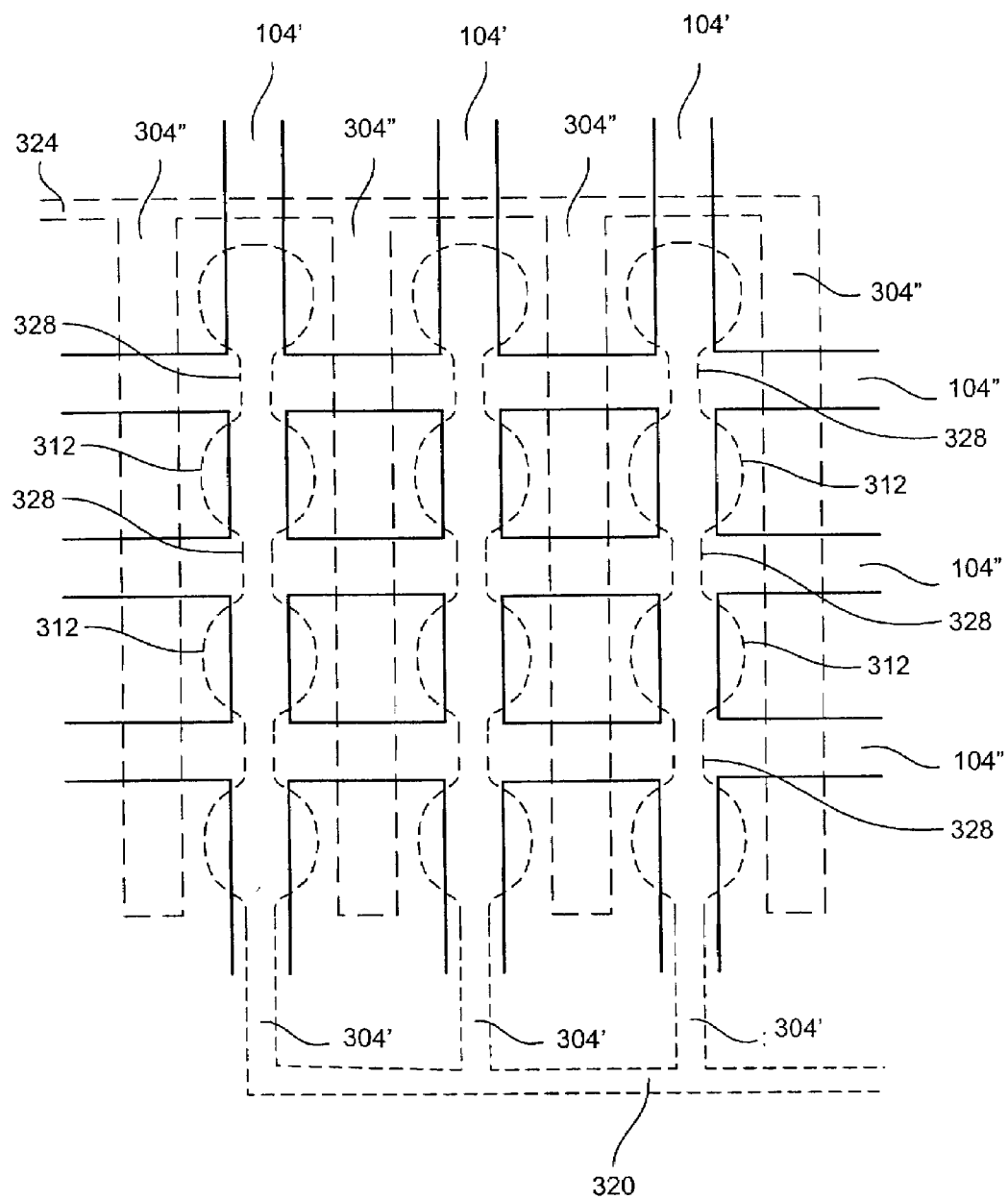
FIG. 5 is a schematic illustration of a microfluidic device having a first plurality of control channels for controlling flow within the first plurality of flow channels and a second plurality of control channels for controlling flow within the second plurality of flow channels.

As shown in FIG. 5, in one particularly embodiment, all of the first set of flow channels 104' are controlled by a first plurality (i.e., set) of control channels 304'. Each of the control channels 304' can have a separate inlet or an actuation method. For simplicity in design and actuation, the first plurality of control channels typically has one pressure inlet 320 with a manifold to provide pressure to all of the first set of control channels 304'. In addition, a second set of control channels 304" controls all of the second set of flow channels 104". The second set of control channels 304" has a pressure inlet 324 with a manifold to provide pressure to all of the second set of control channels 304". In this manner, when pressure is applied to the first set of pressure channels 304', the large width portions 312 deflect downward and close off the first set of flow channels 104' preventing introduction of reagents into the first set of flow channels 104.' At the same time, no actuation force is applied to the second set of pressure channels 304" thereby allowing reactive reagents to be introduced into the second plurality of flow channels 108 while preventing introduction of reactive reagents into the first set of flow channels 104'. Thus, undesired cross-contamination is avoided. Similarly, closure of the second set of flow channels 104' by actuating the second set of control channels 104' allows introduction of reagents into the first set of flow channels 104' without any leakage or contamination into the second set of flow channels 104".

Figure 6:
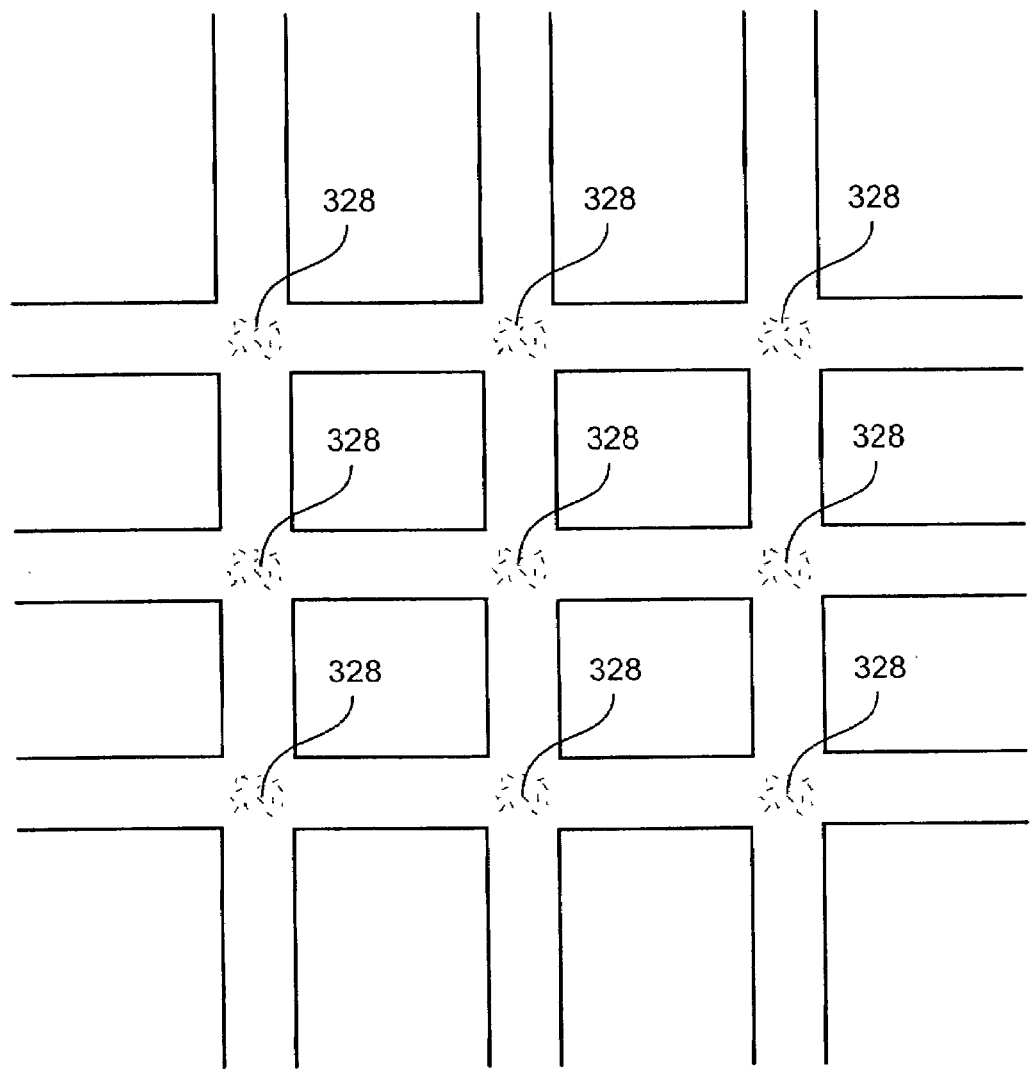
FIG. 6 is a schematic illustration of solid support with an array of compounds produced in the intersections of the first plurality of flow channels and the second plurality of flow channels.

Thus, reactions between two different reagents occur only at the intersections of the first plurality of flow channels 104 and the second plurality of flow channels 108. In this manner, an array of compounds can be synthesized in the plurality of flow channel intersections 328. See FIG. 6. It should be appreciated that monomers can become attached to the entire length of the flow channels. However, only the intersections 328 are exposed to reagents that are introduced from both the flow channels 104' and 104". If desired, monomer bonding at flow channel sections other than the intersections 328 can be reduced or prevented by capping or derivatizing these portions of the solid support.

In one particular embodiment of the present invention, the control channels are controlled by two pressure channel inlets. In this manner, one pressure channel inlet controls all of the flow channels in the first set of flow channels and the other pressure channel inlet controls all of the flow channels in the second set of flow channels. This provides simplicity of controlling fluid flow using only two different control systems, which is particularly useful in combinatorial synthesis. For example, one can close off all of the first set of flow channels and add desired monomer(s) to the second set of flow channels. One can then close off all of the second set of flow channels and add another monomer to the first set of flow channels. By repeating these steps, polymerization of monomers in the intersections of the first set of flow channels and the second set of flow channels can be achieved.

Solid Support

Microfluidic devices of the present invention allow synthesis of an array of compounds on a solid support. Therefore, any material which can be derivatized to allow attachment of a monomer, or a linker molecule, can be used as the solid support. Examples of suitable solid supports include, but are not limited to, glass (including controlled-pore glass), polymers (e.g., polystyrene, polyurethane, polystyrene-divinylbenzene copolymer (e.g., for synthesis of peptides)), silicone rubber, quartz, latex, a derivatizable transition metal (e.g., gold), silicon dioxide, silicon nitride, gallium arsenide, and a derivative thereof, and the like. Except for the reactive sites on the surface, solid support materials are generally resistant to the variety of chemical reaction conditions to which they may be subjected.

Individual planar solid supports can have varied dimensions from which a plurality of individual arrays or chips can be fabricated. The terms "array" and "chip" are used to refer to the final product of the individual array of polymers, having a plurality of spatially distinct polymer sequences coupled to the surface of the solid support. The size of a solid support is generally defined by the number and nature of arrays that will be produced from the solid support. For example, more complex arrays, e.g., arrays having all possible polymer sequences produced from a basis set of monomers and having a given length, will generally utilize larger areas and thus employ larger solid support, whereas simpler arrays may employ smaller surface areas, and thus, smaller solid support. Typically, however, the solid support dimensions can be anywhere from about 1 cm×1 cm to about 30 cm×30 cm.

Elastomeric Materials

The elastic layer of microfluidic devices of the present invention can be fabricated from a wide variety of elastomers. In an exemplary aspect, elastomeric layers can be fabricated from fluoroelastomers, polyurethanes, isoprene polymers, and preferably silicone rubber. However, other suitable elastomers can also be used. It should be appreciated that the present invention is not limited to these types or even families of polymers; rather, nearly any elastomeric polymer is suitable.

In the case of multilayer soft lithography, layers of elastomer are cured separately and then bonded together. This scheme requires that cured layers possess sufficient reactivity to bond together. The elastomeric layers can be of the same type that are capable of bonding to themselves (A to A), or they can be of two different types that are capable of bonding to each other (A to B). (Another possibility is to use an adhesive between layers.)

Given the tremendous diversity of polymer chemistries, precursors, synthetic methods, reaction conditions, and potential additives, there are a huge number of possible elastomer systems that could be used to make chemical reaction apparatus of the present invention. Variations in the materials used will most likely be driven by the need for particular material properties, i.e., solvent resistance, stiffness, gas permeability, temperature stability, and/or reasonable adhesion to the solid support.

There are many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones (e.g., GE RTV 615).

The elastomer can be doped or coated with a coating material to provide reactive sites or to provide chemical resistance. Such chemical resistance is useful to reduce or prevent elastomer from reacting with reagents or dissolving in the solvent. One can coat the elastomer with a fluoropolymer (e.g., Teflon® or CYTOP™ (Asahi Glass Company)), Vitrinite® Protective Coating (MetroLine Surfaces, Inc.), which generally involves depositing a flexible glass-like coating by a CVD (chemical vapor deposition) process, polypropylene, polyvinylidene fluoride, Viton® or other suitable inert materials. In addition, the elastomer can be coated with a thick layer of silicon dioxide by treating the elastomer derived from a silicone with oxygen plasma. For example, it has been found by the present inventors that a silicon dioxide coating can be prepared on GT RV615 polymer by exposing the polymer to oxygen plasma (e.g., 30 min. to 2 hours).

The surface of the elastic layer can be made inert to solvents by flowing a solution of coating material in a solvent through the flow channel to deposit such material along the inner surface of the flow channels. Alternatively, the surface of elastic layer(s) can be modified by chemical treatment or plasma etching to modify the surface directly or to prepare it to receive a coating such as those described above. A coating material can be poured, sprayed, spin-coated, brushed, evaporated, plasma deposited, or flowed through the channels to coat the inner surface of the channels. Alternatively, parts of the elastomeric layer(s) can be dipped or soaked in a solution to apply the coating material.

V. Sheath Flow Process

In another aspect of the present invention is illustrated in FIGS. 7A–7D, where control channels are omitted for clarity. In one particular embodiment, the flow channel configurations and the solvent are selected such that the Reynold's number of the system is low resulting in laminar solvent flow. Thus, when two fluids are introduced into a flow channel 712 side by side, there is no significant turbulent mixing. There may be some mixing of fluids by diffusion; however, when a sufficiently fast fluid flow rate is maintained, fluids travel through the flow channel 712 before any significant mixing by diffusion occurs. This method differs from a hydrodynamic focussing process in that no actual focussing is used.

Figure 7A:
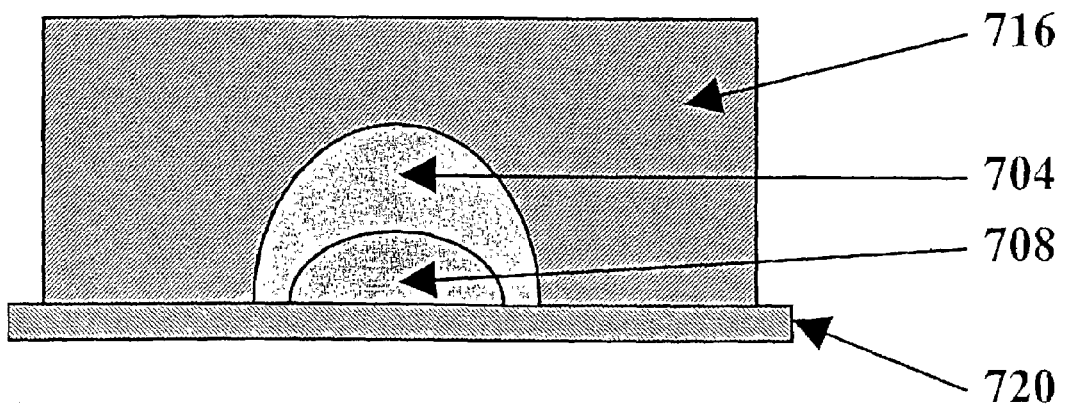
FIGS. 7A–7D illustrate Sheath Flow process of the present invention.
Figure 7B:
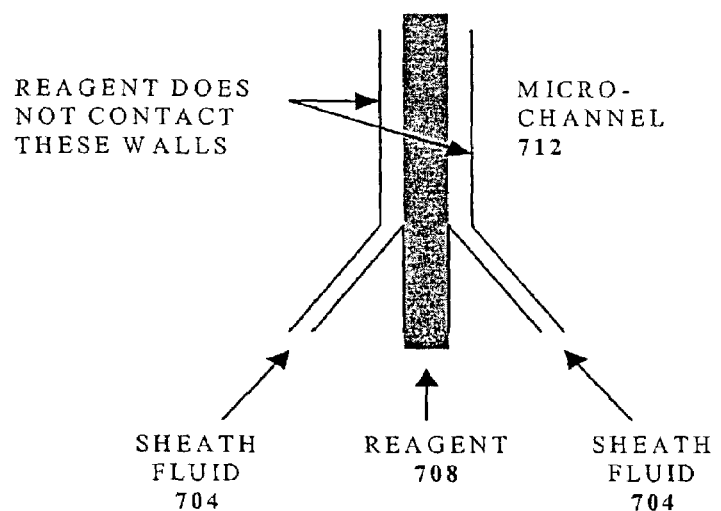
Figure 7C:
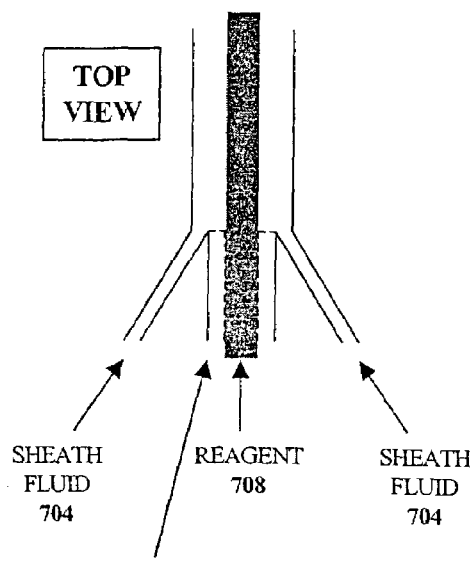
Figure 7D:
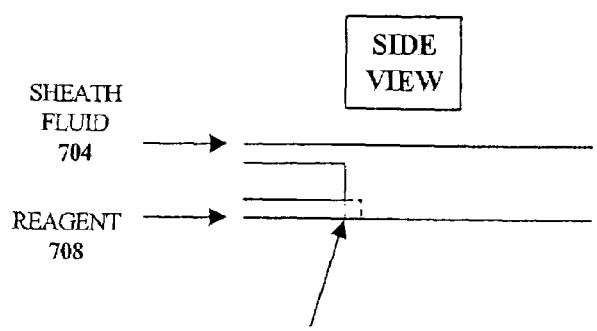

As illustrated in FIG. 7A, the sheath flow (i.e., laminar flow) process ensures that the sheath flow solvent (i.e., sheath fluid) 704 remains substantially separate from the reaction mixture 708 in the flow channel 712. By introducing the sheath fluid 704 and the reaction mixture (i.e., reagent or solvent) 708 at a particular manner, for example, as shown in FIGS. 7B and 7C, one can substantially reduce or eliminate contact between the reaction mixture 708 and the elastomeric layer 716. Typically, the sheath fluid 704 and the reaction mixture 708 are introduced in a direction similar to the direction of the output flow, as illustrated in FIGS. 7B and 7C. The sheath fluid 704 is introduced simultaneously or continuously adjacent to both sides of the reaction mixture 708. In addition, to prevent or reduce the reaction mixture 708 from contacting the upper wall of the channel, i.e., elastomeric material 716, additional sheath fluid is introduced via a wider channel above the reaction mixture injection channel.

Preferably, the sheath fluid 704 is selected such that it is compatible with both the elastomer material 716 and the reaction mixture 708. Therefore, with this technique, any elastomer material that is compatible with the sheath fluid 704 can be used. Accordingly, the elastomeric material 716 need not be chemically resistant to the reaction solvent.

As shown in FIG. 7A, as the reaction mixture 708 flows through the flow channel, it maintains contact with the solid support 720, thereby allowing reaction to occur between the reactive reagent in the reaction mixture and the functional group on the solid support or the solid support-bound compound.

VI. Methods for Conducting Combinatorial Synthesis

Addition of Reagents Into the Flow Channels

Generally, any conventional methods for introducing reagents into the flow channel can be used. Typically, however, a standard medical Luer stub (with a size that is larger than the fluid flow channel size) is attached to the flow channel. The Luer stub typically remains in place by static friction and/or partial adhesion to the elastomer. A tubing or a syringe is then attached to the Luer stub for injection and/or extraction of the fluids into the flow channel. Alternatively, HPLC fittings can be used instead of a Luer stub. In general, the inner diameter of the HPLC fittings (or the Luer stub) is aligned with the flow channel.

If the flow channel has closed end edges, a preferred method for introducing a reagent into the fluid flow channels is to make (e.g., punch) holes in the flow channels up through the elastomer and out the top surface (alternatively, the holes can be made in the solid support), place Luer stubs into these holes, and attach tubing or syringes, or a similar device to the Luer stubs for injection and/or extraction of the fluids. The holes can also be made by embedding wires or other rigid structures in the elastomer while it is being cured, and removing the wires to leave a hole after the elastomer has fully cured.

Fluids are generally introduced through a tubing under pressure (e.g., pushed through by pressurized gas such as nitrogen or argon) or by using a syringe. The amount of pressure required to introduce the fluid depends on many factors, such as the viscosity of the fluid, as well as being limited by the adhesion strength of the elastic layer to the solid support. However, the elastic layer(s) can be held onto the solid support mechanically, for example, by a clamp, to permit high pressures. Alternatively, the fluid is introduced via a pipette and flows due to capillary forces.

In some embodiments, peristaltic pump(s), which are formed from control channel(s), can be used to transport the fluid to and from the flow channel. Such embodiments are advantageous when a particularly small amount of fluid is used.

After introduction of each reagent into the flow channel, the flow channel can be washed with a solvent prior to introduction of another reagent. This minimizes any contamination reaction from a non-solid support-bound reagent.

Stripping and Rinsing

In order to ensure efficiency and accuracy in synthesizing polymer arrays, it is generally desirable to provide a clean solid support surface upon which the various reactions are to take place. Accordingly, in some processing embodiments of the present invention, the solid support is stripped to remove any residual dirt, oils or other materials which may interfere with the synthesis reactions.

The process of stripping the substrate typically involves applying, immersing or otherwise contacting the solid support with a stripping solution. Stripping solutions may be selected from a number of commercially available, or readily prepared chemical solutions used for the removal of dirt and oils, which solutions are well known in the art. Particularly preferred stripping solutions include Nanostrip® and a mixture of concentrated $H_2O_2$ and $NH_4OH$. Gas phase cleaning and preparation methods may also be applied to the solid support using techniques that are well known in the art.

Derivatization

In some embodiments, after the solid support surface has been cleaned and stripped, the surface is derivatized to provide other sites or functional groups on the solid support surface for synthesizing the various polymer sequences. In particular, derivatization provides reactive functional groups, e.g., hydroxyl, carboxyl, amino groups or the like, to which the first monomer(s) or linker(s) in the polymer sequence can be attached. In one particular embodiment, the solid support surface is derivatized using silane in either water or ethanol. Preferred silanes include mono- and dihydroxyalkylsilanes, which provide a hydroxyl functional group on the surface of the solid support. Also preferred are aminoalkyltrialkoxysilanes which can be used to provide the initial surface modification with a reactive amine functional group. Particularly preferred are 3-aminopropyltriethoxysilane and 3-aminopropyltrimethoxysilane ("APS"). Derivatization of the solid support surface using these latter amino silanes provides a linkage that is stable under synthesis conditions and final deprotection conditions (for oligonucleotide synthesis, this linkage is typically a phosphoramidite linkage, as compared to the phosphodiester linkage where hydroxyalkylsilanes are used). Additionally, this amino silane derivatization provides several advantages over derivatization with hydroxyalkylsilanes. For example, the aminoalkyltrialkoxysilanes are inexpensive and can be obtained commercially in high purity from a variety of sources, the resulting primary and secondary amine functional groups are more reactive nucleophiles than hydroxyl groups, the aminoalkyltrialkoxysilanes are less prone to polymerization during storage, and they are sufficiently volatile to allow application in a gas phase in a controlled vapor deposition process. Other suitable linkers are well known to one of ordinary skill in the art.

Additionally, silanes can be prepared having protected or "masked" hydroxyl groups and which possess significant volatility. As such, these silanes can be readily purified, e.g., by distillation, and can be readily employed in gas-phase deposition methods of silanating solid support surfaces. After coating these silanes onto the surface of the solid support, the hydroxyl groups may be deprotected with a brief chemical treatment, e.g., dilute acid or base, which will not attack the solid support-silane bond, so that the solid support can then be used for polymer synthesis. Examples of such silanes include acetoxyalkylsilanes, such as acetoxyethyltrichlorosilane, acetoxypropyl-trimethoxysilane, which may be deprotected after application, e.g., using vapor phase ammonia and methylamine or liquid phase aqueous or ethanolic ammonia and alkylamines.

The physical operation of silanation of the solid support generally involves dipping or otherwise immersing the solid support in the silane solution. Following immersion, the solid support is generally spun laterally to provide a uniform distribution of the silane solution across the surface of the solid support. This ensures a more even distribution of reactive functional groups on the surface of the solid support. Following application of the silane layer, the silanated solid support may be baked to polymerize the silanes on the surface of the solid support and improve the reaction between the silane reagent and the solid support surface.

The silane solution can also be contacted with the surface of the solid support using controlled vapor deposition methods or spray methods. These methods involve the volatilization or atomization of the silane solution into a gas phase or spray, followed by deposition of the gas phase or spray upon the surface of the solid support, usually by ambient exposure of the surface of the solid support to the gas phase or spray. Vapor deposition typically results in a more even application of the derivatization solution than simply immersing the solid support into the solution.

The efficacy of the derivatization process, e.g., the density and uniformity of functional groups on the solid support surface, can generally be assessed by adding a fluorophore which binds the reactive groups, e.g., a fluorescent phosphoramidite such as Fluoreprime® from Pharmacia, Corp., Fluoredite® from Millipore, Corp. or FAM® from ABI, and looking at the relative fluorescence across the surface of the solid support.

Additional objects, advantages, and novel features of this invention will become apparent to those skilled in the art upon examination of the following examples thereof, which are not intended to be limiting.

EXAMPLES

Example 1

This example illustrates a process for synthesizing an array of all possible DNA 6-mers using a chemical apparatus of the present invention which has one elastomer member. It should be appreciated that the "elastomeric layer" of such an apparatus need not be an elastomer, provided one can obtain a good seal with the solid support either by temporary adhesion or by applying pressure.

Figure 8:
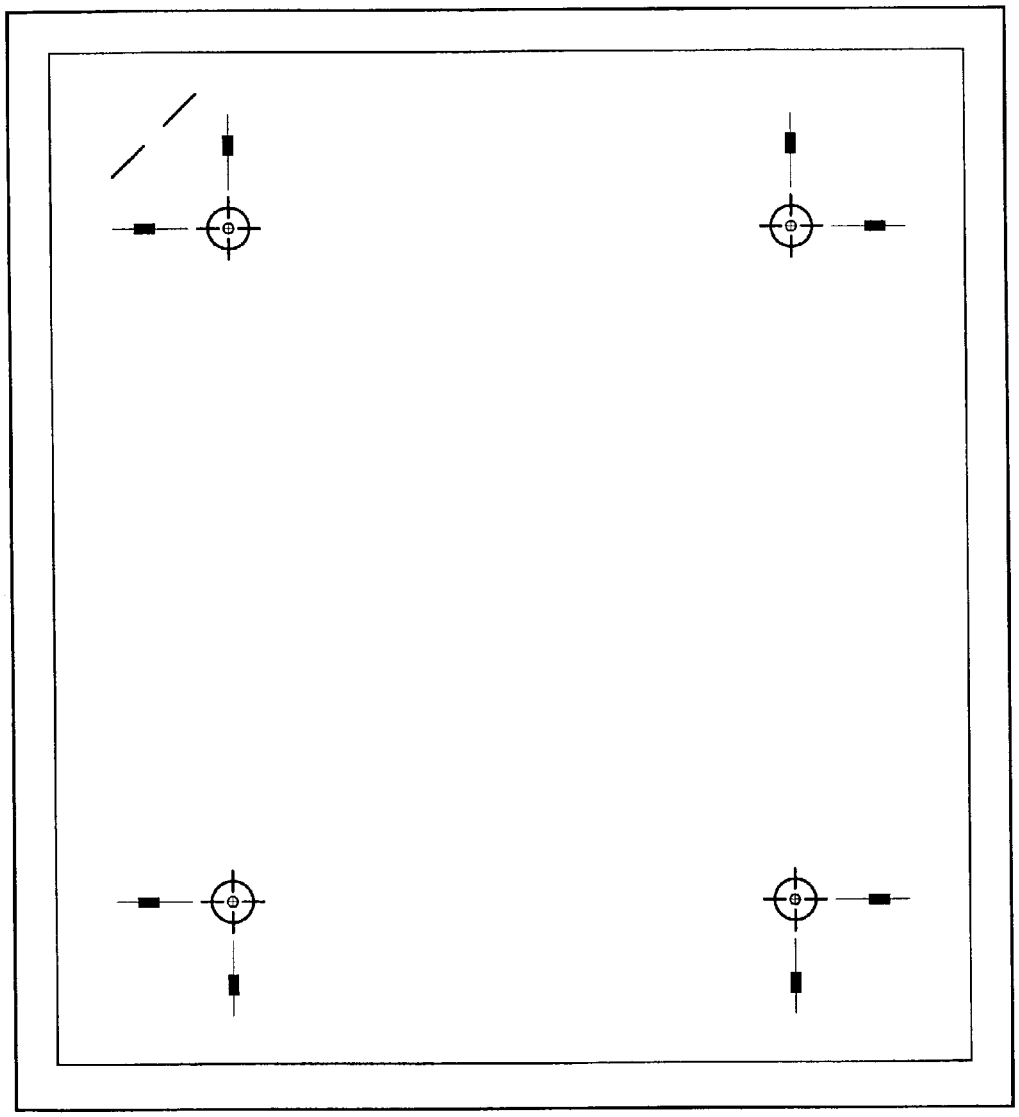
FIG. 8 is a schematic drawing of a mask having four alignment marks near the corners which is etched into the solid support for alignment purposes as illustrated in Example 1, where the two short diagonal lines in the upper left hand corner are "orientation marks"

The solid support is etched with the pattern shown in FIG. 8 for alignment purposes. There are four alignment marks near the corners. These marks line up with the corresponding alignment marks on patterns shown in FIGS. 9, 10, and 11. The two short diagonal lines in the upper left hand corner are "orientation marks."

Figure 9:
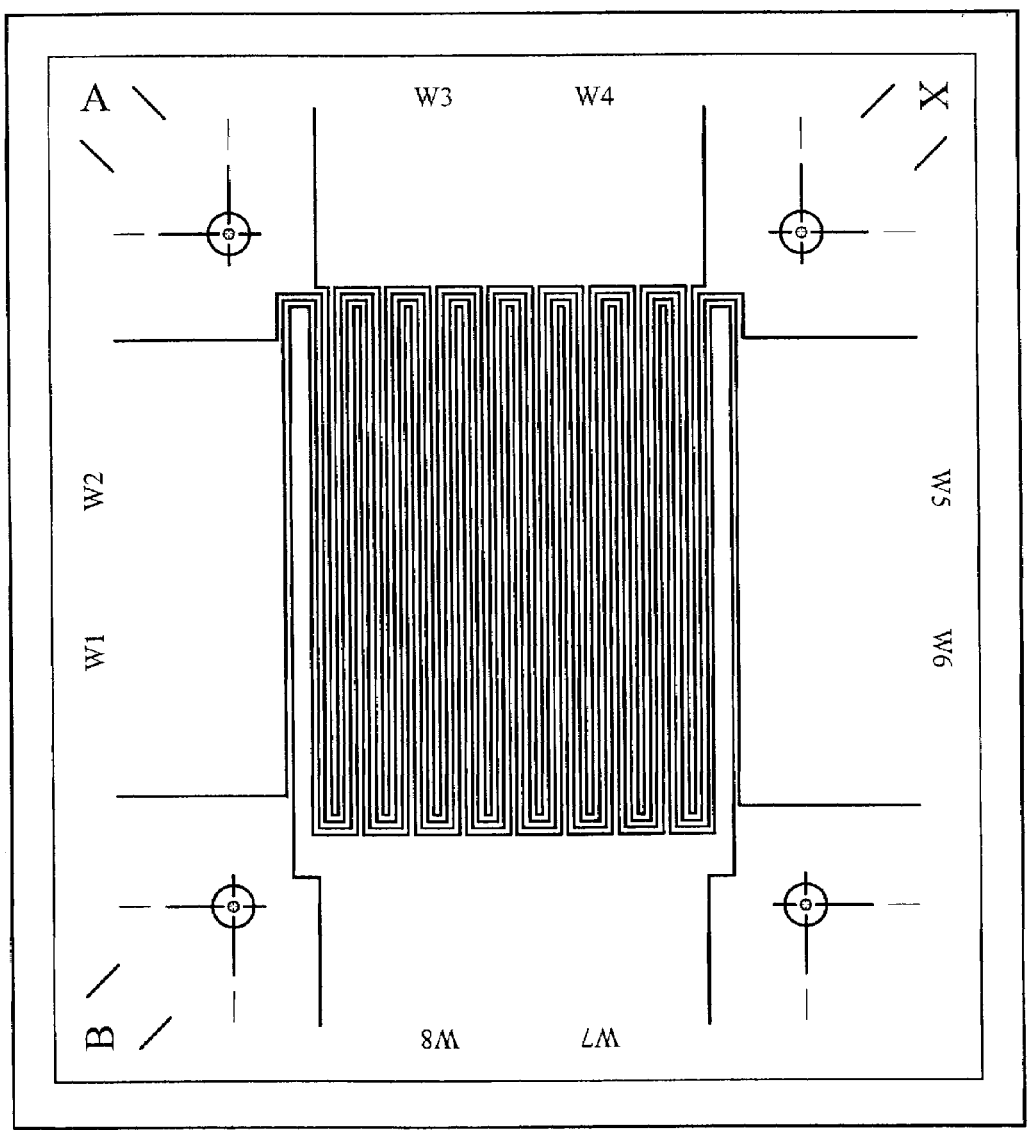
FIGS. 9–11 are schematic drawings of patterns (i.e., masks) which are used to make three molds for three elastomeric layers for a single elastic layer microfluidic combinatorial chemical synthesis device as illustrated in Example 1.
Figure 10:
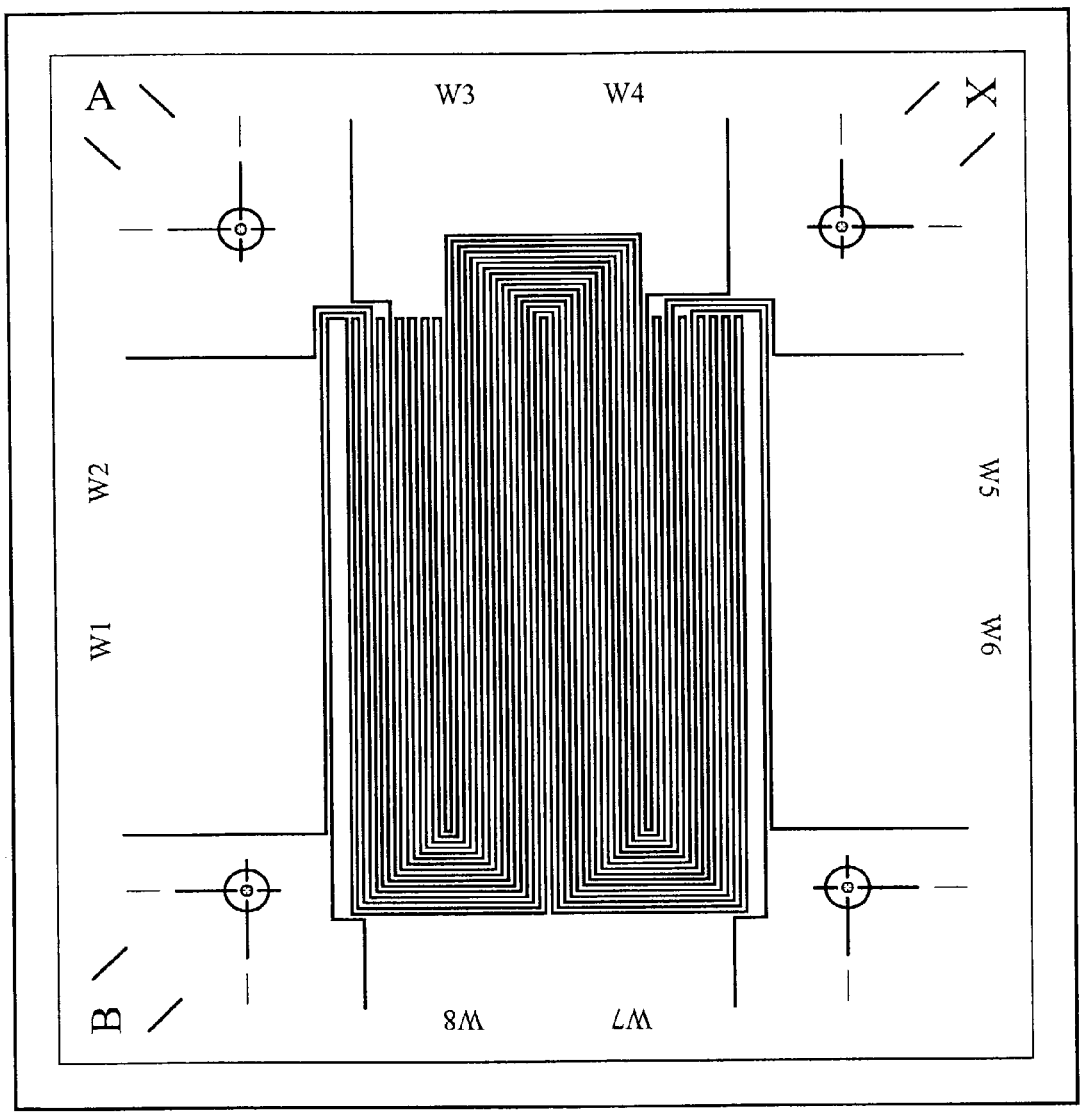
Figure 11:
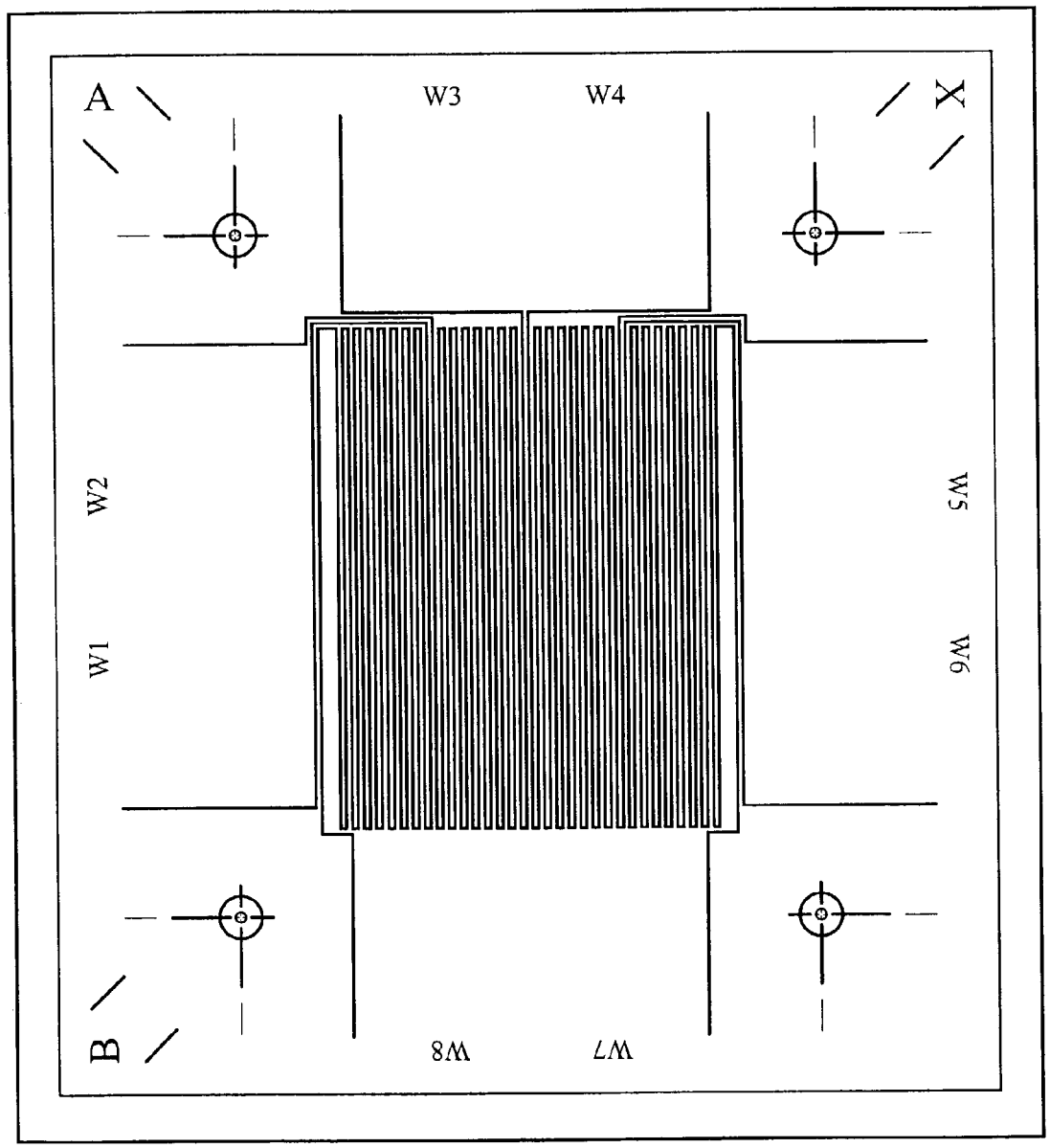

FIGS. 9, 10, and 11 are the patterns that are used to make the molds for elastomer layers. Thus, three elastic layers are made from these molds, i.e., elastic layers 1, 2, and 3 from FIGS. 9, 10, and 11, respectively. Looking down through the top surface of each elastic layer, one can see the pattern exactly as illustrated in these Figures. Centered in each Figure is a dense pattern of flow channels. These channels all terminate abruptly near the edge of the pattern. Each of the three elastomeric layers has four distinct flow channels in it with each flow channels crossing the center section 16 times.

The short diagonal lines in three of the corners (with "A", "B", "X") line up with the short diagonal lines on the solid support. For example, when elastomeric layer 1 is aligned on top of the solid support, there will be two small crosses in the upper left corner, near the 'A' marking. When elastomeric layer 1 is first rotated clockwise by 90 degrees before alignment (solid support never moves), the cross pattern will be close to the 'B' marking. (If the crosses are near the 'X' corner or the blank corner, the orientation is incorrect.) The above orientations of elastomeric layer 1 with respect to the solid support are referred to as the "A-orientation" and "B-orientation," respectively.

In this particular embodiment, holes are punched or drilled through the elastomers near the ends of the channels which can serve as the site for injection. These sites are labeled as W1, W2, ..., and W8. Each of the four channels in each elastomer has only one inlet and one outlet. Thus, if the fluid reaches the outlet, it indicates that the fluid has reached every point in the channel. Otherwise, if fluid flowed through all 16 crossings simultaneously, one would have to watch very carefully that the fluid has made it through all 16 individual paths. However, this latter approach may be preferably if a faster flow rate is desired.

DNA synthesis typically involves 4 general steps: (i) deblocking; (ii) coupling; (iii) capping; and (iv) oxidizing. Steps (i),(iii),(iv) can be accomplished using variety of methods, but for the purposes of this example, by removing the elastomeric layer and immersing the solid support in the relevant reagents. Step (ii) can be generally performed with the elastomer member affixed to the solid support.

Step 1:

The elastic layer 1 (having a pattern shown in FIG. 9) was aligned in the A-orientation with the solid support and then attached thereto. This can be done under a microscope or on a photolithographic mask-aligner. Coupling reagents were then added to the apparatus through the channels such that nucleotide A flowed from W8 to W7, C flowed from W1 to W6, G flowed from W2 to W5, and T flowed from W3 to W4. All the channels were then washed to remove non-attached nucleotides. The elastomeric layer 1 was then removed from the solid support. The resulting solid support was then immersed in a solution comprising a capping reagent to cap the nucleic acids. The capped nucleic acids were then oxidized and deblocked.

During step 1, the following pattern of 64 separate vertical stripes of first nucleotides were thus produced (reading a single row of the array from left to right): AC GTTG-CAACGTTGCAACGTTGCAACGTTGCAACGTTGCA ACGTTGCAACGTTGCAACGTTGCA.

At this point, the solid support is preferably dried with nitrogen or argon.

Step 2:

The elastic layer 1 was aligned in the B-orientation with the solid support. Note that the positions of "W1", "W2", etc. were rotated. Step 2 refers to these new rotated positions. Another set of coupling reagents were then added through the channels such that nucleotide A flowed from W8 to W7, C flowed from W1 to W6, G flowed from W2 to W5, and T flowed from W3 to W4. All the channels were then washed to remove non-attached nucleotides. The elastomeric layer 1 was then removed from the solid support. The resulting solid support was then immersed in a solution comprising a capping reagent to cap the nucleic acids. The capped nucleic acids were then oxidized and deblocked.

Step 2 added a second nucleotide to each array position, this time as uniform horizontal stripes.

Step 3:

The elastic layer 2 (having a pattern shown in FIG. 10) was aligned in the A-orientation with the solid support. Coupling reagents were then added to the apparatus through the channels such that nucleotide A flowed from W8 to W1, C flowed from W2 to W3, G flowed from W4 to W5, and T flowed from W6 to W7. All the channels were then washed to remove non-attached nucleotides. The elastomeric layer 2 was then removed from the solid support. The resulting solid support was then immersed in a solution comprising a capping reagent to cap the nucleic acids. The capped nucleic acids were then oxidized and deblocked.

During step 3, the following pattern of 64 separate vertical stripes of third nucleotides were added (reading a single row from left to right): AAAACCCCGG GGTTTTTTTTGGGGCCCCAAAAAAAAC-CCCGGGGTTTTT TTTGGGGCCCCAAAA Step 4:

The elastic layer 2 was aligned in the B-orientation with the solid support. Another set of coupling reagents were then added through the channels such that nucleotide A flowed from W8 to W1, C flow from W2 to W3, G flow from W4 to W5, and T flowed from W6 to W7. All the channels were then washed to remove non-attached nucleotides. The elastomeric layer 2 was then removed from the solid support. The resulting solid support was then immersed in a solution comprising a capping reagent to cap the nucleic acids. The capped nucleic acids were then oxidized and deblocked.

Step 4 added a fourth nucleotide to each position on the array as horizontal stripes.

Step 5:

The elastic layer 3 (having a pattern shown in FIG. 11) was aligned in the A-orientation with the solid support. Coupling reagents were then added to the apparatus through the channels such that nucleotide A flowed from W8 to W1, C flowed from W2 to W3, G flowed from W4 to W5, and T flowed from W6 to W7. All the channels were then washed to remove non-attached nucleotides. The elastomeric layer was then removed from the solid support. The resulting solid support was then immersed in a solution comprising a capping reagent to cap the nucleic acids. The capped nucleic acids were then oxidized and deblocked.

During step 5, the following set of 64 separate vertical stripes of fifth-nucleotides were thus added (reading a single row from left to right): AAAAAAAA AAAAAAAAC-CCCCCCCCCCCCCCCGGGGGGGGGGGGGGGG GGTTTTTTTTTTTTTTTT Step 6:

The elastic layer 3 was aligned in the B-orientation with the solid support. Another set of coupling reagents were then added through the channels such that nucleotide A flow from W8 to W1, C flowed from W2 to W3, G flowed from W4 to W5, and T flowed from W6 to W7. All the channels were then washed to remove non-attached nucleotides. The elastomeric layer was then removed from the solid support. The resulting solid support was then immersed in a solution comprising a capping reagent to cap the nucleic acids. The capped nucleic acids were then oxidized and deblocked.

Step 6 added a sixth nucleotide at each position on the array in uniform horizontal stripes.

A final deprotection for the whole array was achieved by immersing the entire solid support in a solution comprising a deprotecting reagent.

In this manner, an array of all possible DNA 6-mers was created on a single solid support.

Example 2

This example illustrates a method for synthesizing an array of all possible DNA 4-mers using a microfluidic device of the present invention which includes a solid support with a two-layer elastic device containing valves for controlling the fluid flow.

Figure 12A:
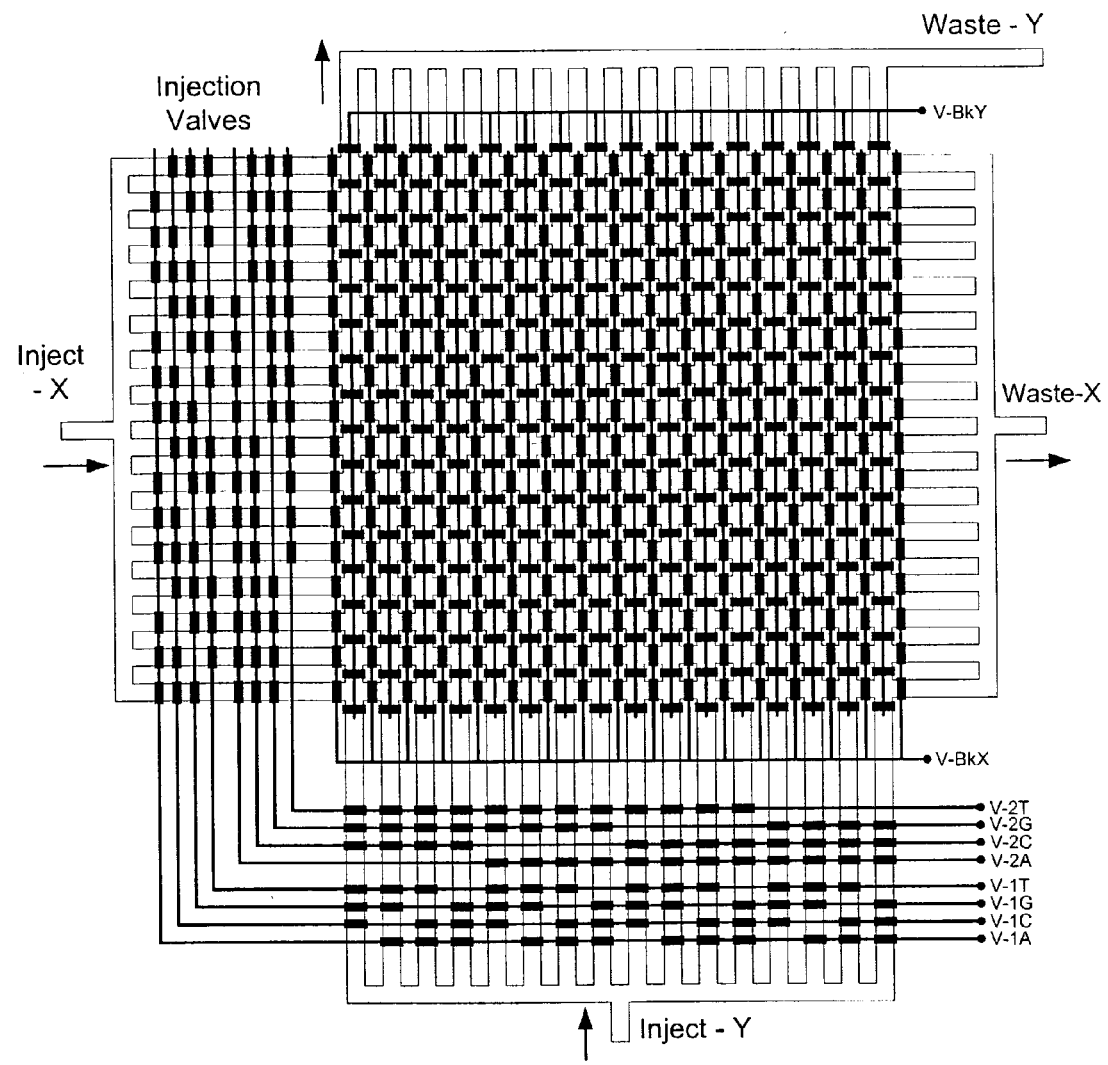
FIG. 12A is a schematic drawing of flow channels (grey) and control channels (black) including valves for a multi elastic layer microfluidic combinatorial chemical synthesis device of the present invention, the use of which is illustrated in Example 2.
Figure 12B:
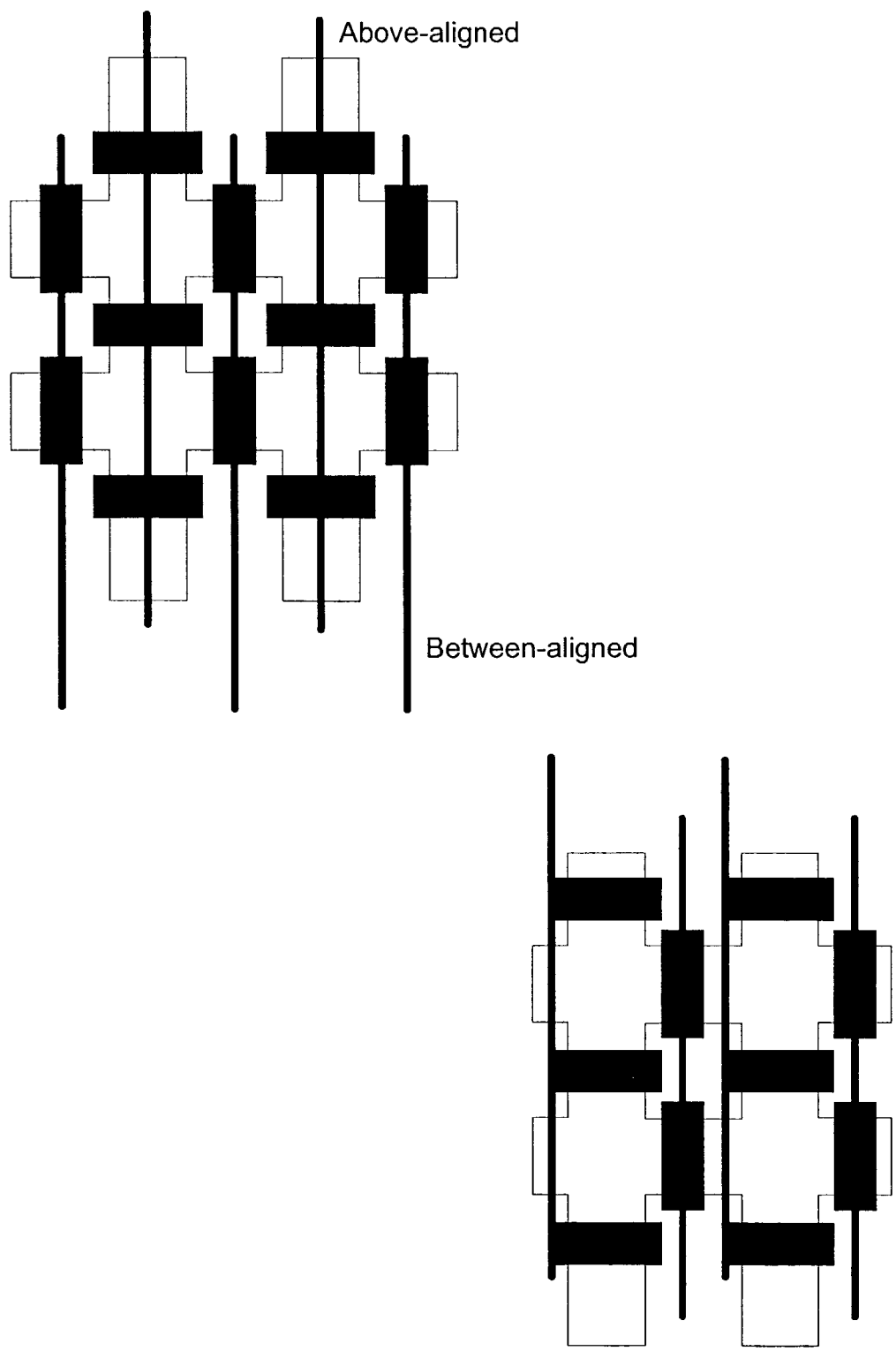
FIG. 12B is a close-up view of a section of FIG. 12A showing two variations of "above-aligned" and "between-aligned" control channels (black) relative to the flow channels (grey). In particular, it illustrates that the narrow parts of the "above-aligned" and "between-aligned" control channels can have any alignment, provided the wide sections are aligned above and between the flow channels, respectively.

The valve array design is shown in FIGS. 12A and 12B. The part in grey is the pattern that is used to make the mold for casting the bottom layer (i.e., the elastic layer) containing the flow channels. The part in black is the pattern from which a mold is made to cast the top layer (i.e., the elastic layer comprising control channels) of the 2 layer elastic apparatus. Note that the way these have been superimposed in the image is similar what one would see, looking down through the device from the top through the two layers towards the solid support.

In this embodiment, no alignment marks are needed because there is no need to remove and reattach the elastomeric layers. The fluid channels essentially consist of two sets of channels. One set of 16 channels flows in the X-direction from left to right (from Inject-X to Waste-X). The other set of 16 channels flows in the Y-direction from bottom to top (from Inject-Y to Waste-Y). In some cases, more valves at the outputs may be needed to ensure that the fluid does not flow in the backward direction. These details have been omitted for clarity.

If the set of control channels connected to V-BlkX (which are on top of the x-axis flow channels and are aligned in between y-axis flow channels) is pressurized, all the channels in the X-direction are blocked, leaving only the Y-direction channels open for flow of reagents. Similarly, if the set of control channels connected to V-BlkY (which are on top of the y-axis flow channels and are aligned in between x-axis flow channels) is pressurized, all the channels in the Y-direction are blocked leaving only the X-direction channels open for flow of reagents. The valves close the underlying fluid channels only when they are wide. The narrow sections of the control channels generally have no significant effect on the underlying flow channel layer.

The remaining set of valves are called injection valves. They control which channels the injected fluid will enter. For clarity and simplicity of illustration, there is only one injection point for the X-direction channels and one for the Y-direction channels. This means that nucleic acids A, C, G, and T have to be introduced sequentially. However, it should be appreciated that reagents can be introduced simultaneously to different channels by having more injection valves, which may or may not be interconnected.

The two elastic layers are attached to a clean derivatized solid support to provide a microfluidic device having flow channel and pressure channel configurations as shown in FIG. 12.

Step 1: First Flow of Reagents in the X-direction Channels

The "V-BlkY" pressure channel is activated (e.g., pressurized with air) to block the flow in the Y-direction and to allow the flow in the X-direction. Injection valve V-1A is activated (e.g., pressurized with air) to allow flow of a solution containing nucleic acid 'A' through channels (rows) 1, 5, 9 and 13, numbered from the top of FIG. 12A, and to block the flow of solution in all other channels in the X-direction. A solution containing nucleic acid 'A' is introduced through Inject-X. The injected reagent exits at waste-X site. The channels are then flushed (i.e., washed) with a wash buffer by injecting the wash solution at Inject-X site.

Injection valve V-1A is deactivated (e.g., by depressurizing), and injection valve V-1C is activated to allow flow of a solution containing nucleic acid 'C' through channels (rows) 2, 6, 10 and 14, and to block the flow of solution in all other channels in the X-direction. The nucleic acid 'C' is then injected through Inject-X. The channels are then flushed with a wash buffer.

Injection valve V-1C is deactivated and injection valve V-1G is activated to allow flow of a solution containing nucleic acid 'G' through channels 3, 7, 11, and 15, and to block the flow of solution in all other channels in the X-direction. A solution containing nucleic acid 'G' is introduced through Inject-X. The channels are then flushed with a wash buffer.

Injection valve V-1G is deactivated and injection valve V-1T is activated to allow flow of a solution containing nucleic acid 'T' through channels 4, 8, 12, and 16, and to block the flow of solution in all other channels in the X-direction. A solution containing nucleic acid 'T' is introduced through Inject-X. The channels are then flushed with a wash buffer.

Figure 13A:
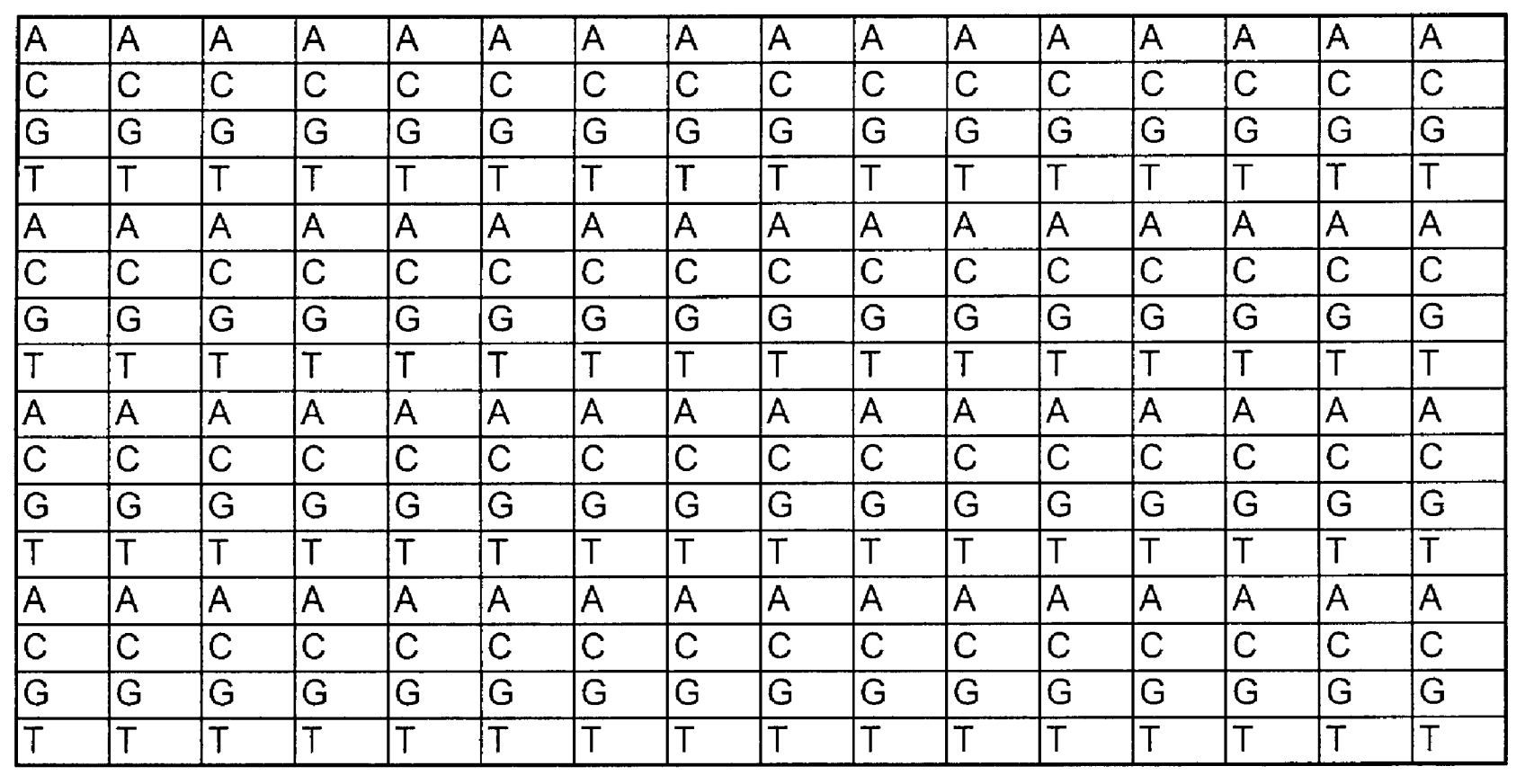

At this point, all 16 X-direction channels have been exposed to coupling reagent only once, i.e., the first base has been added to all 'rows' of the array. FIG. 13A illustrates the nucleotide array composition after Step 1.

Injection valve V-1T is deactivated and a capping reagent is injected through Inject-X to introduce the capping reagent through the entire set of channels in the X-direction. The channels are then flushed with a wash buffer, and an oxidizing reagent is introduced through Inject-X to allow flow of the oxidizing reagent through all the channels in the X-direction. The channels are flushed with a wash buffer, a deblocking reagent is introduced through Inject-X, and the channels are again flushed with a wash buffer.

Step 2: First Flow of Reagents in the Y-direction Channels

The "V-BlkY" pressure channel is deactivated and the "V-BlxX" pressure channel is activated (e.g., pressurized with air) to block the flow in the X-direction and to allow the flow in the Y-direction.

Injection valve V-1A is activated to allow flow of a solution containing nucleic acid 'A' through channels 1, 5, 9, and 13, numbered from the left, and to block the flow of solution in all other channels in the Y-direction. A solution containing nucleic acid 'A' is introduced through Inject-Y. The solution exits through Waste-Y. The channels are then flushed with a wash buffer.

Injection valve V-1A is deactivated and injection valve V-1C is activated to allow flow of a solution containing nucleic acid 'C' through channels 2, 6, 10 and 14, and to block the flow of solution in all other channels in the Y-direction. A solution containing nucleic acid 'C' is introduced through Inject-Y. The channels are then flushed with a wash buffer.

Injection valve V-1C is deactivated and injection valve V-1G is activated to allow flow of a solution containing nucleic acid 'G' through channels 3, 7, 11, and 15, and to block the flow of solution in all other channels in the Y-direction. A solution containing nucleic acid 'G' is introduced through Inject-Y. The channels are then flushed with a wash buffer.

Injection valve V-1G is deactivated and injection valve V-1T is activated to allow flow of a solution containing nucleic acid 'T' through channels 4, 8, 12, and 16, and to block the flow of solution in all other channels in the Y-direction. A solution containing nucleic acid 'T' is introduced through Inject-Y. The channels are then flushed with a wash buffer.

Injection valve V-1T is deactivated and a capping reagent is injected through Inject-Y to introduce the capping reagent through the entire channels in the Y-direction. The channels are then flushed with a wash buffer, and an oxidizing reagent is introduced through Inject-Y to allow flow of the oxidizing reagent through all the channels in the Y-direction. The channels are flushed with a wash buffer, a deblocking reagent is introduced through Inject-Y, and the channels are again flushed with a wash buffer.

Figure 13B:
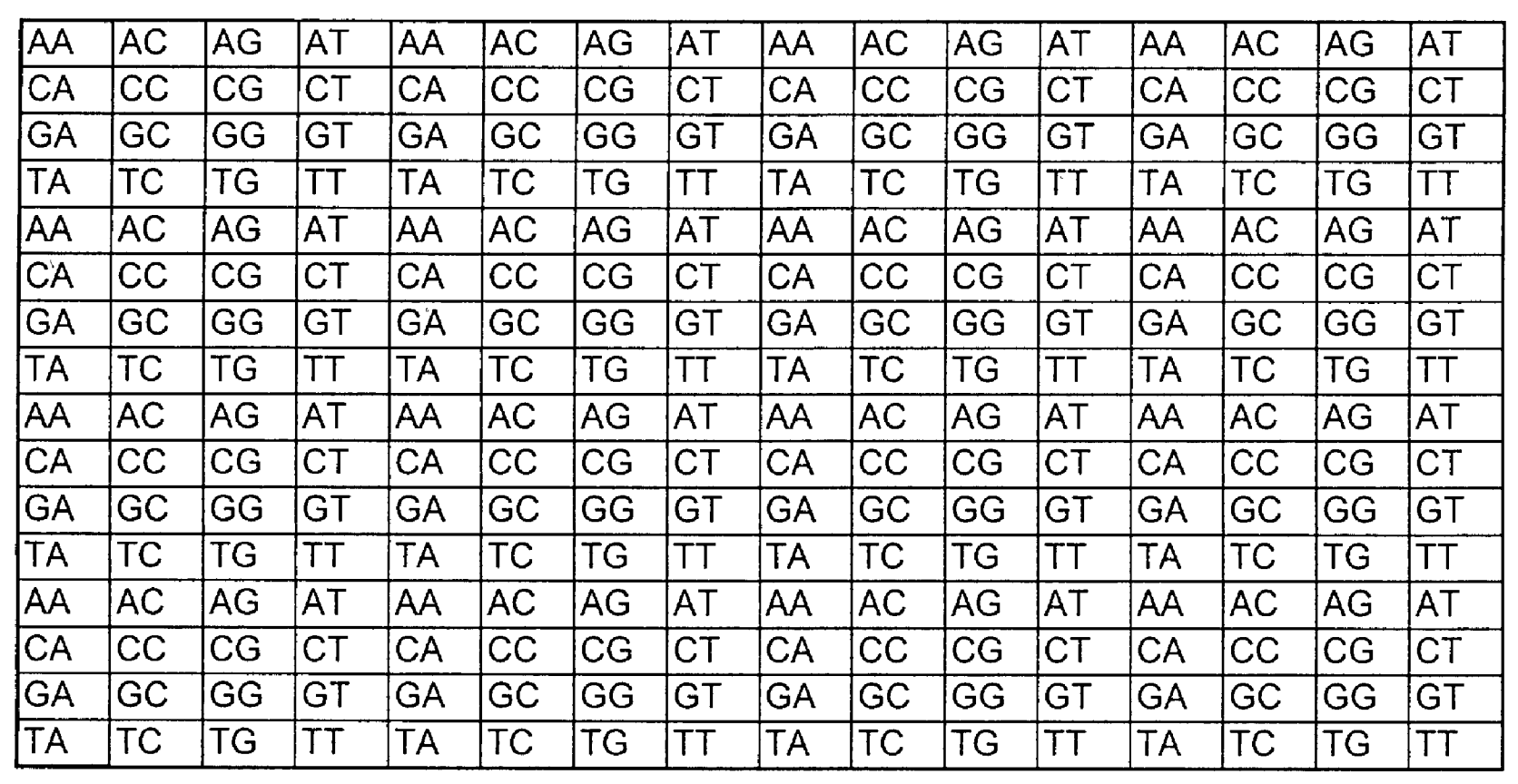

Step 2 adds a second base to all compounds on the array. The second base is the same for all compounds in a given column. FIG. 13B illustrates the nucleotide array composition after Step 2.

Step 3: Second Flow of Reagents in the X-direction Channels

The "V-BlkX" pressure channel is deactivated and the "V-BlkY" pressure channel is activated to block the flow in the Y-direction and to allow the flow in the X-direction. Injection valve V-2A is activated to allow flow of a solution containing nucleic acid 'A' through channels 1, 2, 3, and 4, and to block the flow of solution in all other channels in the X-direction. A solution containing nucleic acid 'A' is introduced through Inject-X. The injected reagent exits at the waste-X site. The channels are then flushed (i.e., washed) with a wash buffer by injecting the wash solution at Inject-X site.

Injection valve V-2A is deactivated, and injection valve V-2C is activated to allow flow of a solution containing nucleic acid 'C' through channels 5, 6, 7 and 8, and to block the flow of solution in all other channels in the X-direction. The nucleic acid 'C' is then injected through Inject-X. The channels are then flushed with a wash buffer.

Injection valve V-2C is deactivated and injection valve V-2G is activated to allow flow of a solution containing nucleic acid 'G' through channels 9, 10, 11, and 12, and to block the flow of solution in all other channels in the X-direction. A solution containing nucleic acid 'G' is introduced through Inject-X. The channels are then flushed with a wash buffer.

Injection valve V-2G is deactivated and injection valve V-2T is activated to allow flow of a solution containing nucleic acid 'T' through channels 13, 14, 15, and 16, and to block the flow of solution in all other channels in the X-direction. A solution containing nucleic acid 'T' is introduced through Inject-X. The channels are then flushed with a wash buffer.

Step 3 adds a third base to all compounds on the array. The third base is the same for all compounds in a given row. FIG. 13C illustrates the nucleotide array composition after Step 3.

Injection valve V-2T is deactivated and a capping reagent is injected through Inject-X to introduce the capping reagent through the entire channels in the X-direction. The channels are then flushed with a wash buffer, and an oxidizing reagent is introduced through Inject-X to allow flow of the oxidizing reagent through all the channels in the X-direction. The channels are flushed with a wash buffer, a deblocking reagent is introduced through Inject-X, and the channels are again flushed with a wash buffer.

Step 4: Second Flow of Reagents in the Y-direction Channels

The "V-BlkY" pressure channel is deactivated and the "V-BlxX" pressure channel is activated to block the flow in the X-direction and to allow the flow in the Y-direction.

Injection valve V-2A is activated to allow flow of a solution containing nucleic acid 'A' through channels 1, 2, 3, and 4, and to block the flow of solution in all other channels in the Y-direction. A solution containing nucleic acid 'A' is introduced through Inject-Y. The solution exits through Waste-Y. The channels are then flushed with a wash buffer.

Injection valve V-2A is deactivated and injection valve V-2C is activated to allow flow of a solution containing nucleic acid 'C' through channels 5, 6, 7, and 8, and to block the flow of solution in all other channels in the Y-direction. A solution containing nucleic acid 'C' is introduced through Inject-Y. The channels are then flushed with a wash buffer.

Injection valve V-2C is deactivated and injection valve V-2G is activated to allow flow of a solution containing nucleic acid 'G' through channels 9, 10, 11, and 12, and to block the flow of solution in all other channels in the Y-direction. A solution containing nucleic acid 'G' is introduced through Inject-Y. The channels are then flushed with a wash buffer.

Injection valve V-2G is deactivated and injection valve V-2T is activated to allow flow of a solution containing nucleic acid 'T' through channels 13, 14, 15, and 16, and to block the flow of solution in all other channels in the Y-direction. A solution containing nucleic acid 'T' is introduced through Inject-Y. The channels are then flushed with a wash buffer.

Injection valve V-2T is deactivated and a capping reagent is injected through Inject-Y to introduce the capping reagent through the entire channels in the Y-direction. The channels are then flushed with a wash buffer, and an oxidizing reagent is introduced through Inject-Y to allow flow of the oxidizing reagent through all the channels in the Y-direction. The channels are flushed with a wash buffer, a deblocking reagent is introduced through Inject-Y, and the channels are again flushed with a wash buffer.

Step 4 adds a fourth base to all compounds on the array. The fourth base is the same for all compounds in a given column. FIG. 13D illustrates the nucleotide array composition after Step 4.

The elastomeric layers are then removed from the solid support. A final deprotection step (e.g., ammonia deprotection) is performed on the whole solid support. The elastomeric layers can be discarded, or reused to make an array on another solid support.

With the example injection valve arrangement shown in FIG. 12A, a total of 4×N/2 injection valves are needed to make a complete library of an array of DNA N-mers. Alternatively, more complicated reaction sequences can be achieved by having a plurality of valves at the waste side which is designed to redirect the flow from selected channels back into other channels flowing in the reverse direction. In this manner, one can achieve a "serpentine" arrangement of flow channels similar to that described in Example 1.

Example 2 is described for a chemical apparatus of the present invention having only one injection point at each axis, i.e., Inject-X and Inject-Y. However, a microfluidic device having a more sophisticated injection system (e.g., having four separate inlets for nucleic acids A, C, G, T, and inlets for the other reagents) is also within the scope of the present invention.

While the present invention has been described herein with reference to particular embodiments thereof, a latitude of modification, various changes and substitutions are intended in the foregoing disclosure. It will be appreciated that in some instances some features of the invention will be employed without a corresponding use of other features without departing from the scope of the invention as set forth herein. Therefore, many modifications may be made to adapt a particular situation or material to the teachings of the invention without departing from the essential scope and spirit of the present invention. It is intended that the invention not be limited to the particular embodiment disclosed as the best mode contemplated for carrying out this invention, but that the invention shall include all embodiments and equivalents falling within the scope of the appended claims.

What is claimed is:

1. A microfluidic combinatorial chemical synthesis device, comprising:
   (a) a first solid support comprising a plurality of microfluidic flow channels formed therein, wherein a reactive functional group for attaching a reactive reagent thereto is attached to a surface of each of the flow channels;
   (b) a second solid support comprising a plurality of control channels formed therein; and
   (c) an elastomeric layer sandwiched between the first and second solid support and disposed such that the flow channels and the control channels are separated by different segments of the elastomeric layer, wherein each elastomeric segment is deflectable into or retractable from the fluid flow channel that it overlays in response to an actuation force applied to one of the control channels.

2. The microfluidic combinatorial chemical synthesis device of claim 1, wherein the first solid support is comprised of a material selected from the group consisting of glass, polystyrene, polystyrene-divinylbenzene copolymer, silicone rubber, quartz, latex, polyurethane, a derivatizable transition metal, silicon dioxide, silicon nitride, gallium arsenide, and a derivative thereof.

3. The microfluidic combinatorial chemical synthesis device of claim 2, wherein said derivatizable transition metal is gold.

4. The microfluidic combinatorial chemical synthesis device of claim 1, wherein said first solid support is a rigid material.

5. The microfluidic combinatorial chemical synthesis device of claim 4, wherein said second solid support is made from a rigid material.

6. The microfluidic combinatorial chemical synthesis device of claim 5, wherein said elastomeric layer is removeably disposed in between said first and second solid supports such that said elastomeric layer forms a part of said fluid flow channels and said control channels.

7. The microfluidic combinatorial chemical synthesis device of claim 1, wherein at least a portion of said plurality of control channels are aligned in between said fluid flow channels.

8. The microfluidic combinatorial chemical synthesis device of claim 7, wherein at least a portion of said control channels are aligned on top of said fluid flow channels.

9. The microfluidic combinatorial chemical synthesis device of claim 8, wherein each of said control channels aligned on top of said fluid flow channels comprise regions of wider cross-section and regions of narrower cross-section.

10. A method for synthesizing a library of compounds on a microfluidic device, the method comprising:
    (a) providing a microfluidic device comprising a plurality of fluid flow channels defined by an elastomeric layer and a solid support such that the flow channels comprise an elastomeric portion and a solid support portion, wherein the solid support comprises a reactive functional group attached to the inner surface of the flow channels for attaching a reactive reagent thereto;

(b) producing a solid-support bound compound by introducing a reactive reagent into the fluid flow channels under conditions sufficient to covalently attach at least a portion of the first reactive reagent to the reactive functional group;

(c) modifying the solid support-bound compound by introducing another reactive reagent into the fluid flow channels under conditions sufficient to react the solid-support bound compound with the reactive reagent; and (d) optionally repeating step (c), thereby obtaining the library of compounds, and wherein the reactive agent introduced in steps (b)–(d) is introduced by providing a laminar flow of a sheath fluid in between the reactive agent and the elastomeric layer portion of the fluid flow channels, wherein the sheath fluid is compatible with the elastomeric layer.

11. A method for synthesizing a library of compounds on a microfluidic device, the method comprising:

(a) positioning a solid support and an elastomeric layer having a plurality of recesses formed therein with respect to one another to form a first plurality of flow channels, wherein the solid support comprises a plurality of reactive functional groups for attaching a reactive reagent thereto that are attached to an inner surface of at least some of the first flow channels;

(b) producing a solid-support bound compound by introducing a first reactive reagent into one or more of the fluid flow channels under conditions sufficient to covalently attach at least a portion of the first reactive reagent to the reactive functional group;

(c) repositioning the elastomeric layer with respect to the solid support to form a second plurality of flow channels defined by the solid support and the recesses in the elastomeric layer such that the second flow channels intersect the first flow channels;

(d) modifying the solid support-bound compound by introducing a second reactive reagent into one or more of the second fluid flow channels under conditions sufficient to react, the solid-support bound compound with the second reactive reagent.

12. A method for synthesizing a library of compounds on a microfluidic device, the method comprising:

(a) providing a microfluidic device comprising (i) a first solid support comprising a plurality of microfluidic flow channels formed therein, wherein a reactive functional group for attaching a reactive reagent thereto is attached to a surface of each of the flow channels, (ii) a second solid support comprising a plurality of control channels formed therein; and (iii) an elastomeric layer sandwiched between the first and second solid support and disposed such that the flow channels and the control channels are separated by different segments of the elastomeric layer, wherein each elastomeric segment is deflectable into or retractable from the fluid flow channel that it overlays in response to an actuation force applied to one of the control channels;

(b) producing a solid-support bound compound by introducing a reactive reagent into the fluid flow channels under conditions sufficient to covalently attach at least a portion of the first reactive reagent to the reactive functional group;

(c) modifying the solid support-bound compound by introducing another reactive reagent into the fluid flow channels under conditions sufficient to react the solid-support bound compound with the reactive reagent; and (d) optionally repeating step (c), thereby obtaining the library of compounds.

13. The method of claim 12, wherein the fluid flow channels and the control channels are located on the interface of the elastomeric layer and the solid support.

14. The microfluidic combinatorial chemical synthesis device of claim 1, wherein the elastomeric layer is a material that is inert to solvents used in the synthesis of oligonucleotides.

15. The microfluidic combinatorial chemical synthesis device of claim 1, wherein the elastomeric layer is a fluoroelastomer.

* * * * *

UNITED STATES PATENT AND TRADEMARK OFFICE
CERTIFICATE OF CORRECTION

| | |
|---|---|
| PATENT NO. | : 7,097,809 B2 |
| APPLICATION NO. | : 10/116761 |
| DATED | : August 29, 2006 |
| INVENTOR(S) | : Michael Van Dam et al. |

It is certified that error appears in the above-identified patent and that said Letters Patent is hereby corrected as shown below:

Column 1, lines 14-18, delete "The U.S. Government has a paid-up license in this invention and the right in limited circumstances to require the patent owner to license others on reasonable terms as provided for by the terms of Grant No. HG-01642-02, awarded by the National Institutes of Health." and insert --This invention was made with government support under Grant No. HG-01642-02 awarded by the National Institute of Health. The government has certain rights in the invention.--

Signed and Sealed this

Fourteenth Day of April, 2009

JOHN DOLL
*Acting Director of the United States Patent and Trademark Office*